US008936466B2

(12) United States Patent
Moffson et al.

(10) Patent No.: US 8,936,466 B2
(45) Date of Patent: Jan. 20, 2015

(54) DENTAL IMPLANTATION SYSTEM AND METHOD

(75) Inventors: Allen M. Moffson, Solana Beach, CA (US); Majid Azmoon, Cardiff-by-the-Sea, CA (US)

(73) Assignee: Precision Through Imaging, LLC, Solana Beach, CA (US)

( * ) Notice: Subject to any disclaimer, the term of this patent is extended or adjusted under 35 U.S.C. 154(b) by 0 days.

(21) Appl. No.: 13/554,267

(22) Filed: Jul. 20, 2012

(65) Prior Publication Data
US 2013/0017507 A1 Jan. 17, 2013

Related U.S. Application Data

(63) Continuation of application No. PCT/US2011/022290, filed on Jan. 24, 2011.

(60) Provisional application No. 61/297,389, filed on Jan. 22, 2010.

(51) Int. Cl.
*A61C 3/00* (2006.01)
*A61C 1/08* (2006.01)
(Continued)

(52) U.S. Cl.
CPC ....... *A61C 8/0089* (2013.01); *A61B 2019/5259* (2013.01); *A61B 2019/462* (2013.01);
(Continued)

(58) Field of Classification Search
CPC ............... A61C 1/082–1/084; A61C 5/025; A61B 17/176
USPC .................. 433/27, 72, 74–76, 215, 102–135
See application file for complete search history.

(56) References Cited

U.S. PATENT DOCUMENTS 4,824,367 A 4/1989 Rosenstiel et al.
5,688,118 A * 11/1997 Hayka et al. .................... 433/27
(Continued)

FOREIGN PATENT DOCUMENTS

DE 199 02 273 A1 8/2000

OTHER PUBLICATIONS

European Search Report issued in International Patent Application No. JHC/P204355 EP, dated Jul. 24, 2013, 7 pages.*
(Continued)

*Primary Examiner* — Edward Moran
(74) *Attorney, Agent, or Firm* — Kilpatrick Townsend & Stockton LLP

(57) ABSTRACT

Drilling of an implant shaft is carried out with a handpiece tool whose location and angular orientation with respect to a radiographic working guide is updated in real time with respect to the radiographic working guide and anatomical structures of the patient, free of viewing obstructions. Prior to the drilling, the radiographic working guide is fitted to a particular patient. Real-time imaging support is provided on a display of a computer, wherein the radiographic workpiece guide includes a plurality of fiducial markers that define a substantially planar reference surface of the radiographic workpiece guide. The radiographic workpiece guide also includes an alignment structure located a predetermined distance from a pilot hole proximate the work site. The image is updated based on an initial radiographic scan and updated position information from the handpiece tool as to location and angular orientation of the handpiece tool relative to the workpiece guide.

10 Claims, 13 Drawing Sheets

(51) Int. Cl.
*A61C 8/00* (2006.01)
*A61B 19/00* (2006.01)
*A61B 17/34* (2006.01)

(52) U.S. Cl.
CPC ....... *A61B2017/3407* (2013.01); *A61B 19/201* (2013.01); *A61C 1/084* (2013.01); *A61B 2019/204* (2013.01); *A61B 2019/5466* (2013.01); *A61B 2019/5287* (2013.01)
USPC .................. 433/75; 433/27; 433/72; 433/131

(56) References Cited

U.S. PATENT DOCUMENTS

| | | | |
|---|---|---|---|
| 6,000,939 A | 12/1999 | Ray et al. | |
| 6,319,006 B1 | 11/2001 | Scherer et al. | |
| 6,351,662 B1 | 2/2002 | Franck et al. | |
| 6,529,765 B1 | 3/2003 | Franck et al. | |
| 6,640,128 B2* | 10/2003 | Vilsmeier et al. | 600/427 |
| 6,665,948 B1* | 12/2003 | Kozin et al. | 33/833 |
| 6,786,896 B1 | 9/2004 | Madhani et al. | |
| 7,097,451 B2* | 8/2006 | Tang | 433/76 |
| 7,206,626 B2 | 4/2007 | Quaid, III | |
| 7,346,417 B2 | 3/2008 | Luth et al. | |
| 2002/0133095 A1 | 9/2002 | Mushabac | |
| 2004/0157188 A1* | 8/2004 | Luth et al. | 433/75 |
| 2005/0116673 A1* | 6/2005 | Carl et al. | 318/432 |
| 2005/0163342 A1* | 7/2005 | Persky | 382/103 |
| 2005/0228256 A1 | 10/2005 | Labadie et al. | |
| 2006/0127848 A1* | 6/2006 | Sogo et al. | 433/173 |
| 2006/0142657 A1* | 6/2006 | Quaid et al. | 600/424 |
| 2006/0240378 A1 | 10/2006 | Weinstein et al. | |
| 2008/0318187 A1 | 12/2008 | Wilkinson | |
| 2009/0228031 A1 | 9/2009 | Ritter et al. | |
| 2009/0253095 A1* | 10/2009 | Salcedo et al. | 433/75 |

OTHER PUBLICATIONS

International Search Report and Written Opinion of the International Searching Authority issued in PCT/US11/22290, dated Apr. 5, 2011, 8 pages.

Brief et al. "Accuracy of image-guided implantology" Clin. Oral. Impl. Res. 16, 2005, 495-501.

* cited by examiner

DENTAL IMPLANTATION SYSTEM AND METHOD

CROSS-REFERENCES TO RELATED APPLICATIONS

This application is a continuation of PCT/US2011/022290, filed Jan. 24, 2011, which in turn claims priority from provisional U.S. patent application Ser. No. 61/297,389, titled "Dental Implantation System and Method" and filed Jan. 22, 2010, the entire disclosures of which are hereby incorporated herein and for all purposes.

BACKGROUND OF THE INVENTION

Dental implant surgery involves placing a prosthetic device such as one or more artificial replacement teeth in the mouth of a patient. Such prosthetic devices must be precisely placed in the mouth for the best aesthetic and functional results. Precise placement of the prosthetic device requires suitable preparation of the implant site with respect to surrounding tissue and bone. The prosthetic device typically comprises a tooth implant abutment, a pontic attached thereto, and a tooth implant fixture that extends from the abutment and is received into an implant shaft drilled into the patient's bone with a drilling tool (e.g., dental handpiece). During the drilling of bone to create the implant shaft, great care must be taken to avoid causing injury to the patient. Injury may be caused by, for example, inadvertent entry into the mandibular nerve canal, inadvertent entry into the sinuses, perforation of the cortical plates, damage to adjacent teeth, or other damage known in the art.

Systems that provide real-time imaging of implant sites can be helpful to the implant practitioner is avoiding injury to patients and in more accurately preparing the bone, implant site, and preparation of the shaft for receiving the implant. Conventional systems that provide such imaging can be cumbersome, complicated, and difficult to use. Moreover, the images provided by systems that rely on optical (viewable) images can be limited by images that are obscured by fluids, including blood and water found at the implant site during drilling. In addition, some computer-assisted imaging systems are not especially accurate in determining location of anatomical structures and instruments, nor are they especially accurate in updating such location information in real-time during the drilling procedure.

Improved real-time imaging would assist the implant practitioner with precise location of the drilling tool during the procedure and would benefit the patient by reducing the risk of injury and helping to provide an effective implant. Such techniques could also be used in a variety of procedures, beyond the dental field, including, for example, other health practices and non-medical procedures.

What is needed is improved real-time imaging support for dental implant surgery. Embodiments of the invention satisfy this need.

BRIEF SUMMARY OF THE INVENTION

In one aspect, a computer method is provided. The method comprises receiving data from a sensor system on a dental handpiece that comprises a handpiece drill. The sensor system engages a known surface of a workpiece guide affixed to a dental arch of a patient. The method further comprises determining, based at least in part on the data from the sensor system, the location and angular orientation of the handpiece drill in relation to features of the workpiece guide, and generating a display image at a computer. The generated display image includes an image of the patient's dentition and a depiction of the location and angular orientation of the handpiece drill in relation to the patient's dentition. For example, an image of the patient's dentition may have been previously obtained using a CT scan or other technique, and vectors, lines, or other indicators may be overlaid on the image to depict the location and angular orientation of the handpiece drill. The method also includes receiving updated data from the sensor system on the dental handpiece, determining from the updated data an updated location and angular orientation of the handpiece in relation to the patient's dentition, and adjusting the display image to show the updated location and angular orientation of the handpiece in relation to the patient's dentition. In this way, real time feedback may be shown indicating how the drill relates to the patient's dentition. In some embodiments, the method further includes receiving an indication that the dental handpiece is registered with features of the workpiece guide. For example, a dentist using the handpiece may place the handpiece in position, and then actuate a switch or otherwise send a signal to the computer system performing the method that the handpiece is registered. The system may also recognize automatically that the handpiece is registered. The method may include generating in the display image an indication of the location and angular orientation of the handpiece drill in relation to a desired implant shaft. For example, the implant shaft location and orientation may have been previously determined from the image of the patient's dentition, and correlated with the features of the radiographic workpiece guide. In some embodiments, the method further includes comparing the location and angular orientation of the handpiece drill with the desired implant shaft, and providing a signal when the location or angular orientation of the handpiece drill differs from that of the desired implant shaft by more than a predetermined amount. The signal may comprise one or more signals selected from the group consisting of a visual cue and a sound cue, alone or in any combination. For example, if the drill begins to depart from the desired implant shaft location and angular orientation, the system may change the color of the depiction on the display screen, may emit an audible warning signal, or may provide a combination of signals. An audible warning could be a simple warning tone, or could include a recorded or synthesized voice. In some embodiments, the sensor system includes a plurality of sensors, each of the sensors including a movable portion and a sensing element that characterizes the position of the movable portion, and in the method, determining, based at least in part on the data from the sensor system, the location and angular orientation of the handpiece drill in relation to the features of the workpiece guide comprises determining the location and angular orientation based at least in part on the positions of the movable portions.

In another embodiment, real-time imaging support is provided by obtaining an initial image of a radiographic workpiece guide on a display of a computer, wherein the radiographic workpiece guide includes a plurality of fiducial markers that define a substantially planar reference surface of the radiographic workpiece guide. The radiographic workpiece guide also includes an alignment structure located a predetermined distance from a pilot hole proximate the work site. The initial image depicts the fiducial markers and alignment structure, and also depicts a desired implant shaft relative to the work site. The implant shaft can receive, for example, the body of a dental implant fixture. A handpiece for drilling the implant shaft is registered such that handpiece data is provided to the computer to define a location and angular orientation of the handpiece relative to the alignment structure and the reference surface. A display image is generated comprising the initial image and a depiction of location and angular orientation of the handpiece relative to the alignment structure and the planar reference surface. Updated handpiece data is determined that define an updated location and angular orientation of the handpiece relative to the alignment structure and the planar reference surface, and the display image is adjusted to show the updated location and angular orientation of the handpiece relative to the alignment structure and the planar reference surface.

In another aspect, a computer system is provided, comprising an image processor that receives an image of a patient's dentition, and a location system that receives data from a sensor system on a dental handpiece that includes a handpiece drill. The sensor system engages a known surface of a workpiece guide fixed to a dental arch of a patient, and the location system determines based at least in part on the data from the sensor system a location and angular orientation of the handpiece drill in relation to the patient's dentition. The computer system also includes a viewer that generates a display image at a computer display such that the generated display image comprises the image of the patient's dentition and a depiction of the location and angular orientation of the handpiece drill relative to the patient's dentition as determined by the location system. The location system receives updated sensor data and determines based at least in part on the updated sensor data an updated location and angular orientation of the handpiece drill in relation to the patient's dentition, and the viewer adjusts the generated display image to show the updated location and angular orientation of the handpiece drill relative to the patient's dentition. In this way, real time feedback may be provided to the user of the handpiece. In some embodiments, the location processor further receives an indication that the dental handpiece is registered with features of the workpiece guide, and the location system determines the location and angular orientation of the handpiece drill based at least in part on the registration of the handpiece with the features of the workpiece guide. In some embodiments, the sensor system includes a plurality of sensors that each includes a sensor tip such that the sensor tips are independently extensible relative to the dental handpiece, and the data from the sensor system indicates the extensions of the sensor tips relative to the dental handpiece, and the location system determines the location and angular orientation of the handpiece drill based at least in part on the extension of each sensor tip. The generated display image may further comprise a depiction of the location and angular orientation of the handpiece drill relative to a desired implant shaft. The location system may determine updated handpiece data in response to receiving data from the sensor system substantially in real time. The computer system may further comprise a computer processor that performs operations of the location system and image processor. The computer processor may perform operations of the viewer.

In another embodiment, there is provided a computer system that includes an image processor that receives an initial image of a radiographic workpiece guide, wherein the radiographic workpiece guide encompasses an implant site, and the initial image depicts a plurality of fiducial markers of the radiographic workpiece guide such that the fiducial markers define a substantially planar reference surface of the radiographic workpiece guide, and wherein the initial image depicts an alignment structure located a predetermined distance from a pilot hole proximate the implant site and a desired implant shaft relative to the work site. The computer system further includes a location system that receives registration information for the handpiece such that the registration information provides handpiece data that defines a location and angular orientation of the handpiece relative to the alignment structure and the substantially planar reference surface. The computer system further includes a viewer that generates a display image at a computer display such that the generated display image comprises the initial image and a depiction of the location and angular orientation of the handpiece relative to the alignment structure and the substantially planar reference surface. The location system determines updated handpiece data that defines an updated location and angular orientation of the handpiece relative to the alignment structure and the substantially planar reference surface, and the viewer adjusts the generated display image to show the updated location and angular orientation of the handpiece relative to the alignment structure and the substantially planar reference surface on the computer display.

In another aspect, an attachment for a dental handpiece is provided. The attachment comprises a fitting configured to engage with the dental handpiece and fix the attachment in relation to the dental handpiece. The attachment further includes a sensor system held in spaced relation to the fitting. The sensors cooperate to provide data that characterize the depth and angular orientation of a handpiece drill comprised in the dental handpiece, the depth and angular orientation being measured in relation to a known surface engaged by the sensor system. The attachment also includes an electronic interface that communicates the data to another system. The fitting may comprise a snap fitting. In some embodiments, each sensor comprises a linearly movable portion and a sensing element that characterizes the position of the movable portion, and the data comprises indications of the positions of the movable portions. Each sensing element may comprise a linear encoder. In some embodiments, the sensors, when the attachment is attached to the dental handpiece, surround the handpiece drill with each sensor substantially parallel to the handpiece drill. The attachment may be disposable. The electronic interface may comprise a universal serial bus (USB) interface.

In another aspect, a method of preparing a dental implant site is provided. The method comprises providing a dental handpiece that includes a handpiece drill, and providing an attachment for the dental handpiece. The attachment includes a sensor system that provides data characterizing the depth an angular orientation of the handpiece drill in relation to a known surface engaged by the sensor system, and the attachment enables the collection of data that characterize the depth and angular orientation of the handpiece drill in relation to the implant site. The method further includes fixing the attachment to the dental handpiece, drilling an implant shaft at the dental implant site using the data from the sensor system to guide the drilling, removing the attachment from the dental handpiece, and disposing of the attachment such that the attachment is used in relation to only one dental patient. Providing the attachment may comprise providing an attachment that includes an electronic interface to communicate the data to another system.

In another aspect, a radiographic workpiece guide is provided. The radiographic workpiece guide comprises a dental arch portion that conforms substantially to a dental arch of a particular patient, a reference surface of the dental arch portion positioned substantially over an implant site encompassed by the dental arch portion, and at least three non-collinear radioopaque fiducial markers on the reference surface. The reference surface may be substantially planar. The radioopaque fiducial markers may identify and locate a top surface of the dental arch portion. In some embodiments, the radiographic workpiece guide further comprises an alignment structure located, when the radiographic workpiece guide is engaged with the dental arch of the particular patient, on the dental arch portion a predetermined distance from the centerline of a desired implant shaft. In some embodiments, the alignment structure comprises a detent that receives a sensor tip of a handpiece having a handpiece drill bit with a central axis, such that the predetermined distance from the alignment structure to the pilot hole is substantially equal to the sensor tip-to-drill bit central axis distance. In some embodiments, the dental arch portion defines a pilot hole located, when the radiographic workpiece guide is engaged with the dental arch of the particular patient, substantially at the centerline of a desired implant shaft.

According to another embodiment, there is provided a radiographic workpiece guide which includes a dental arch portion that conforms substantially to a patient dental arch and encompasses an implant site of the patient. The radiographic workpiece guide further includes a substantially planar reference surface of the dental arch portion that includes at least three non-collinear radioopaque fiducial markers, such that the radioopaque fiducial markers identify and locate a top surface of the dental arch portion. The radiographic workpiece guide further includes an alignment structure located a predetermined distance from a centerline on the dental arch portion that indicates a desired centerline of a dental implant to be received at the implant site.

According to another aspect, a method is provided, comprising fabricating a radiographic workpiece guide of a configuration to engage a dental arch of a particular patient and encompass an implant site. The radiographic workpiece guide includes a reference surface substantially over the implant site, and the method further includes placing at least three non-collinear radioopaque fiducial markers on the reference surface. In some embodiments, the method further comprises engaging the radiographic workpiece guide with the dental arch of the patient, obtaining a radiographic image of the workpiece guide and the patient's dental arch, the radiographic image depicting the fiducial markers, determining from the radiographic image the location of a desired implant shaft for placing an implant at the implant site, and correlating the location of the desired implant shaft with the locations of the fiducial markers. The method may further include forming a pilot hole in the radiographic workpiece guide, wherein the centerline of the pilot hole will be substantially collinear with the centerline of the implant shaft when the radiographic workpiece guide is engaged with the patient's dental arch, and placing an alignment structure on the reference surface. In some embodiments, the method further comprises registering a dental handpiece comprising a handpiece drill to the reference surface, the pilot hole, and the alignment structure, obtaining data from sensors on the dental handpiece, determining, based at least in part on the data, the position and angular orientation of the handpiece drill in relation to the desired implant shaft, displaying, on a visual display, at least a portion of the radiographic image showing the patient's dentition, and simultaneously displaying, on the visual display, an indication of the position and angular orientation of the handpiece drill in relation to the patient's dentition as shown on the display. The method may further comprise simultaneously displaying, on the visual display, an indication of the position and angular orientation of the handpiece drill in relation to the desired implant shaft. In some embodiments, the method further comprises generating a signal when the location or angular orientation of the handpiece drill differs from that of the desired implant shaft by more than a predetermined amount.

According to another aspect, a method is provided comprising engaging a radiographic workpiece guide with the dental arch of a particular patient. The radiographic workpiece guide is of a configuration to engage a dental arch of the patient and encompass an implant site, and the radiographic workpiece guide includes a reference surface substantially over the implant site and at least three non-collinear radioopaque fiducial markers on the reference surface. The method further comprises obtaining a radiographic image of the workpiece guide and the patient's dental arch, the radiographic image depicting the fiducial markers, determining from the radiographic image the location of a desired implant shaft for placing an implant at the implant site, and correlating the location of the desired implant shaft with the locations of the fiducial markers.

According to another aspect, a system is provided comprising an attachment for fixing to a dental handpiece that comprises a handpiece drill. The attachment comprises a sensor system that generates data usable to determine the position and angular orientation of the handpiece drill in relation to a reference surface engaged by the sensor system. The system further includes a workpiece guide of a configuration to engage a dental arch of a patient. The workpiece guide includes a known reference surface over an implant site and features for registering the sensor system to the workpiece guide. The system further comprises a computer system comprising a processor and a display, and an electronic interface that communicates the data from the sensor system to the computer system. In use, the sensor system is registered to the features of the workpiece guide and the sensor system engages the known reference surface of the workpiece guide, and the computer system receives the data from the sensor system, determines the position and angular orientation of the handpiece drill in relation to the patient's dentition based at least in part on the data from the sensor system, and displays, on a display, a display image that depicts the position and angular orientation of the handpiece drill in relation to the patient's dentition. In some embodiments, the set of sensors comprises at least three sensors, each including a linearly movable portion and generating data that indicates the position of the respective linearly movable portion. The display image may comprise a previously-obtained radiographic image of the patient's dentition. In some embodiments, the computer system updates the display image substantially in real time as the dental handpiece is moved. The display image may further depict the position and angular orientation of the handpiece drill in relation to a desired implant shaft. In some embodiments, the system further comprises the dental handpiece.

In another aspect, there is provided a plurality of alignment sensors within a drill alignment sensor sub-assembly that can be attached to a drill for a non-medical use. The plurality of alignment sensors are connected to a computer system that includes a location system that receives information on the extension of the alignment sensors. The computer system further includes a display that provides real-time information on the depth and orientation of the drill bit relative to a surface articulated by the alignment sensors.

In another aspect, there is provided a method for accurately drilling a hole using a drill for a non-medical use in combination with a drill alignment sensor sub-assembly and a computer system connected thereto. The method includes affixing the drill alignment sensor sub-assembly to the drill for a non-medical use, positioning the resulting combination above a non-medical workpiece into which a hole will be drilled, and drilling the hole. Extension information from the alignment sensors is received by the computer system, which in turn provides a real-time display of the orientation and depth of the drill bit.

Other features and advantages should be apparent from the following description of exemplary embodiments, which illustrate, by way of example, aspects of the invention.

BRIEF DESCRIPTION OF THE DRAWINGS

FIG. 8A demonstrates an embodiment wherein the centerline of the desired implant shaft is overlaid with the real-time position of the drill. FIG. 8B demonstrates an embodiment wherein the centerline and desired bore width of the implant shaft is overlaid with the real-time position of the drill.

DETAILED DESCRIPTION OF THE INVENTION

Definitions

Figure 1A:
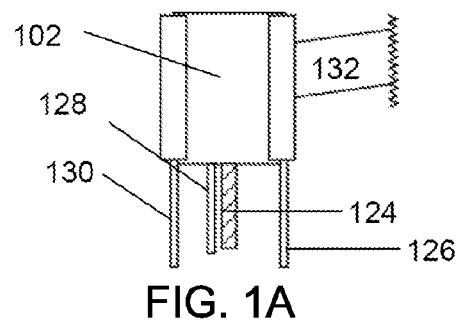
FIGS. 1A-1C show a system including a workpiece guide 104, handpiece sensor assembly 102, and computer 106 with display 108 constructed in accordance with embodiments of the invention.

Unless expressly defined, the terms used herein have meanings as customarily used in the dental and medical arts.

The terms "implant," "dental implant" and the like (noun), refer in the customary sense to a permanently placed (i.e., non-removable) prosthetic device which includes an artificial tooth root replacement. In some embodiments, the implant includes an implant fixture which is embedded in bone and undergoes integration (i.e., osseointegration) to form a stable integrated structure capable of supporting an artificial tooth or providing support for another dental structure including, for example but not limited to, an implant-support bridge or implant-supported denture, as known in the art. The implant fixture is joined to an implant abutment, typically near the gingival surface, to which implant abutment can be affixed a replacement tooth (i.e., pontic). The term "implant" (verb) refers in the customary sense to the placement of a dental implant. "Implant fixture" refers to that portion of a dental implant which is embedded in bone or other hard tissue or material and which serves to anchor the implant, as known in the art.

The term "patient" refers to a recipient of dental attention, care, or treatment. In some embodiments, a patient is a mammal, for example a human, but a patient may also be an animal other than a human.

The term "dentition" refers to the arrangement of teeth in the mouth. An image of a patient's dentition may show all or part of the patient's dentition, and need not depict all of the patient's teeth.

"Radiographic guide" refers in the customary sense to a removable prosthetic guide capable of being rigidly affixed within the mouth of a patient to the upper or lower dental arch and having one or more radioopaque markers affixed thereto, the location of which can be determined by a plurality of radiographic images, for example in a 3-dimensional ("3-D") radiographic image. Radiographic guides are typically formed on an impression of the patient's dentition and/or other structural features of the mouth by methods well known in the art. Radiographic guides are typically fabricated from a variety of materials, including but not limited to, thermosetting and light-setting plastics, acrylic, and the like, as known in the art.

"Radiographic workpiece guide," "workpiece guide" and the like refer to a radiographic guide suitable to encompass (i.e., affix near) an implant work area, and that additionally includes at least a drill reference surface that includes at least three non-collinear radioopaque fiducial markers affixed thereto. The radiographic workpiece guide affixes to an upper or lower dental arch of the patient. The radiographic workpiece guide is typically fabricated of material, for example but not limited to dental acrylic as known in the art, which is sturdy enough to withstand deformation during subsequent process steps, including drilling in the mouth.

"Working radiographic workpiece guide" refers to a radiographic workpiece guide that includes at least an alignment structure and a drill access, as defined herein. If the alignment structure and drill access are added to a radiographic workpiece guide that does not have such features, then the radiographic workpiece guide prior to the additions may be referred to as an "initial radiographic workpiece guide". The at least three radioopaque markers affixed to the drill reference surface may be the only radioopaque markers on the initial radiographic workpiece guide. In some embodiments, the initial radiographic workpiece guide includes other radioopaque markers in addition to the at least three non-collinear radioopaque markers on the drill reference surface. The terms "radiographic workpiece guide" and "workpiece guide" used without further qualification refer to either of an initial radiographic workpiece guide or a working radiographic workpiece guide.

The terms "radioopaque marker," "radioopaque fiducial marker," "fiducial marker" and the like refer in the customary sense to a deposit of radioopaque material on and/or within, for example, a radiographic guide, capable of being located in a radiographic image.

"Implant site" refers to an oral site capable of receiving, or having received, an implant.

"Implant work area" refers to an implant site and adjacent tissue including adjacent teeth. Radiographic workpiece guides typically encompass the implant work area.

"Alignment structure" refers to a structure of a radiographic workpiece guide that is capable of locating a handpiece relative to the implant site. The alignment structure may take the form of a detent in the radiographic workpiece guide proximate the drill reference surface such that the handpiece can be registered at the alignment structure to a known location. Preferably, the tip of an alignment sensor is received into the detent thereby identifying the position of the alignment sensor at the alignment structure. Multiple alignment structures can be present. In some embodiments, a plurality of alignment sensor tips are each received into one of a plurality of alignment structures.

"Drill reference surface," "planar reference surface" and the like refer to a substantially flat area of an initial or working radiographic workpiece guide, generally perpendicular to the long axis of a desired implant shaft, and adjacent the drill access, which area is capable of articulating at least three handpiece alignment sensors. In some embodiments, the plane of the planar reference surface may deviate from perpendicularity with respect to the long axis of a desired implant shaft, e.g., by about 1, 2, 3, 4, 5, 10, 15, 20, 25 or even 30 degrees. Unless expressly described differently, the term "about" in the context of a numerical value indicates a margin of +/−10% of the numerical value.

"Drill access" refers to a void in a working radiographic workpiece guide adjacent an implant site through which a dental instrument, including a registered handpiece, can be operated at the implant site.

"Prepared implant site" refers to an implant site that has been drilled to afford an implant shaft, optionally tapped, and otherwise prepared as known in the art to receive an implant fixture. "Implant drill shaft," "implant shaft" and the like in the context of dental implantation refer to a hole which is formed to receive an implant fixture. "Desired implant shaft," "proposed implant shaft" and the like refer to the location (i.e., position, depth and angular orientation relative to anatomical structures of the patient identified e.g., in a 3-D scan image) of an implant shaft to be drilled.

"Handpiece" and "dental handpiece" refer in the customary sense to a dental drill suitable for drilling dental tissue. In some embodiments, a dental handpiece may include a handle, a handpiece head, a drill engine contained therein, and a handpiece drill attached to the drill engine.

"Handpiece drill" refers in the customary sense to a dental drill having a drill shaft, optionally a drill shaft extension, and a drill tip. Types of drill tip include burr, conical, twist and the like, as known in the art.

"Handpiece handle" refers in the customary sense to the handle of a dental handpiece.

"Handpiece drill engine" refers in the customary sense to a component of the handpiece providing rotary action to turn the handpiece drill. A variety of handpiece drill engine drive types are known in the art, including but not limited to air, electrical, and mechanical drives.

"Handpiece alignment sensor" refers to a sensor that is operationally coupled to a handpiece and a location system, and which is capable of providing depth and angular location information to the location system. A variety of alternative configurations of the handpiece and alignment sensors are available. In some embodiments, the alignment sensors are integrated into the handpiece head. In some embodiments, the alignment sensors are removably attachable to the handpiece head. In some embodiments, the alignment sensors are included within a handpiece alignment sensor sub-assembly which can be removably attached to the handpiece head. In each configuration contemplated for the handpiece and alignments sensors, the computer system can receive information in real time about the orientation and depth of the drill tip and provide that information on a display.

"Location system" refers to a system operationally coupled to a handpiece alignment sensor and a display, which location system is capable of receiving depth and angular location information from the handpiece alignment sensors, and providing depth and angular location information for presentation on the display.

"Handpiece-sensor assembly" refers to the combination of a handpiece and one or more handpiece alignment sensors coupled thereto.

A "sensor system" refers to a set of one or more sensors and structure for supporting the sensors. A sensor system may be included in a handpiece-sensor assembly, and when in use, may engage a surface of a workpiece guide. For the purposes of this disclosure, for two elements to "engage" means that the elements are in mechanical contact. For example, the sensor system of FIG. 19 engages with the workpiece guide when the tips of the sensors touch the workpiece guide. The sensor system of FIG. 21A engages the workpiece guide when the lower ring and/or alignment pins touch the workpiece guide.

"Registered handpiece" refers to a handpiece-sensor assembly which location and angular orientation with respect to a radiographic workpiece guide are known to the location system.

"Registered" in the context of a registered handpiece refers to the result of registering a handpiece-sensor assembly, as described herein.

Implantation System Components

Figure 1B:
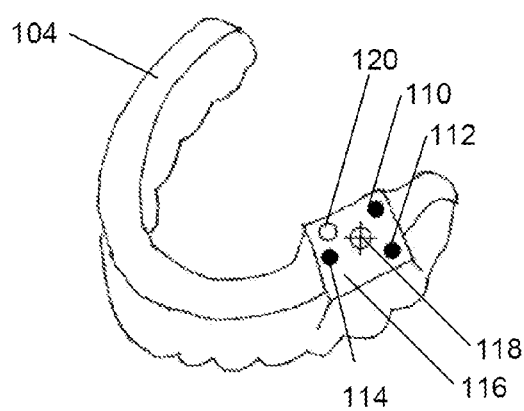
Figure 1C:
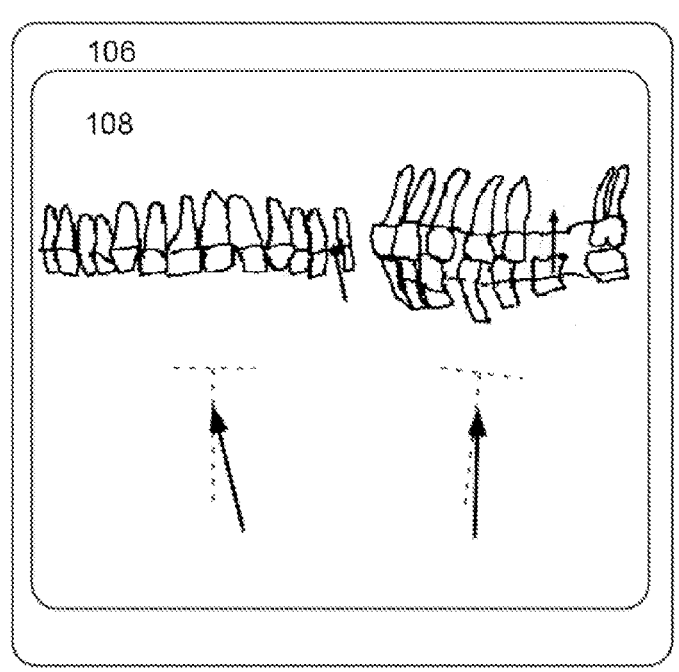

FIGS. 1A-1C show a radiographic workpiece guide 104, handpiece sensor assembly 102, and computer 106 with display 108 constructed in accordance with embodiments of the invention. The radiographic workpiece guide includes fiducial marks 110, 112, 114 that define a substantially planar reference surface 116 of the workpiece guide. Planar reference surface 116 includes a pilot hole 118 that marks the location (drill access) where drilling will take place to provide an implant shaft that receives, for example, the body of a dental implant fixture (not illustrated in FIGS. 1A-1C). The workpiece guide 104 also includes an alignment structure 120 located a predetermined distance from the pilot hole 118.

The handpiece sensor assembly 102 includes a handpiece with a drill 124 and at least three handpiece alignment sensors 126, 128, 130 arranged about the drill, parallel to the long axis of the drill. The handpiece further includes a handpiece handle 132 (partially shown). Preferably, the at least three sensors are equidistance from the drill tip and equally spaced about the drill shaft. The handpiece is registered with the computer 106 such that handpiece data are provided to the computer to define a location and angular orientation of the handpiece relative to the alignment structure 120 and the reference surface 116. Preferably, one of the alignment sensors is received into alignment structure 120 to provide precise positioning thereof. During the implantation procedure, the display 108 is updated by the computer 106 as the handpiece is manipulated so that the display depicts the location and angular orientation of the handpiece relative to the alignment structure and the reference surface, as well as optionally depicting the desired location and angular orientation of the shaft relative to the alignment structure and the reference surface. In some embodiments, the display depicts the fiducial markers 110, 112, 114 and alignment structure 120. In some embodiments, the display additionally provides CT scan image data of the surround dental tissue. The updated display shows the position of the handpiece relative to the reference surface 116 and work site beneath pilot hole 118 such that tissue and fluids (including any tissue and blood, and any site-irrigating water) do not obstruct the imagery. In this way, an implant practitioner can view, in some embodiments, the display 108 and rely on it as the sole source of information regarding the location and angular orientation of the handpiece during the drilling procedure.

In display 108 of FIG. 1C, exemplary frontal maxillary (left) and lateral maxillary and mandibular (right) views of the CT scan image data are displayed. The CT-scan image data, or portions thereof, can be displayed in variety of forms. In the example shown in display 108, only the teeth and roots thereof are displayed. In some embodiments, additional 3-D scan image data are displayed, including but not limited to surrounding dental tissue. Merely for purposes of illustration, the 3-D scan image in FIG. 1C display 108 shows a void at the upper left first adult molar, which is the implant site. Also shown overlaid on the 3-D scan images in display 108 are position sprites, as described herein and further elaborated in FIGS. 8A-B. In some embodiments, the CT scan images can be manipulated (i.e., rotated, translated, scaled) by methods of interactive graphical manipulation known in the art.

Figure 2:
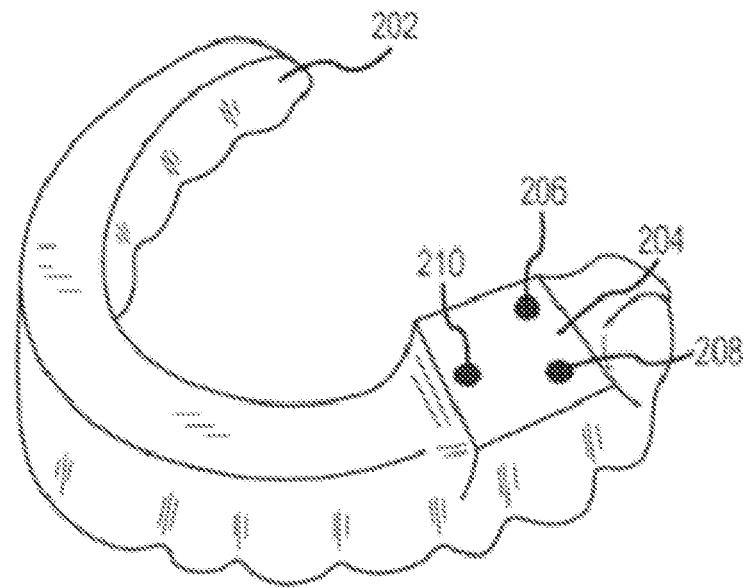
FIG. 2 shows an exemplary initial radiographic workpiece guide in accordance with embodiments of the invention.

FIG. 2 shows an exemplary initial radiographic workpiece guide 202. The initial radiographic workpiece guide has a substantially flat or planar reference surface 204 that includes at least three non-collinear radioopaque fiducial markers 206, 208, 210. The substantially flat reference surface will be referred to herein as the top surface of the radiographic workpiece guide 202 or as being "over" an implant site, though it should be apparent that an initial radiographic guide that is affixed to the lower dental arch will have the flat surface at the top of the guide when the guide is viewed in the patient, whereas an initial radiographic guide affixed to the upper dental arch will have the flat surface at the bottom of the guide, under the implant site, when viewed in the patient. The radioopaque fiducial markers will show as opaque marks in a radiographic scan of the radiographic workpiece guide. The radioopaque fiducial markers identify and locate the top surface 204 to the computer system (FIG. 1C). If the drill reference surface is co-planar with the radioopaque fiducial markers, then the radioopaque fiducial markers also serve to identify and locate the drill reference surface of the initial radiographic workpiece guide during a radiographic scan.

Figure 3:
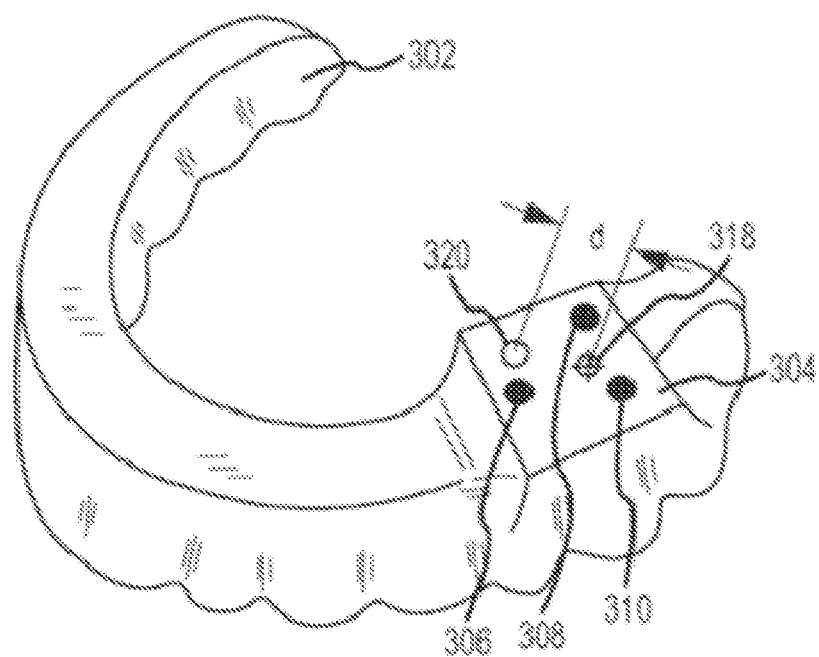
FIG. 3 shows an exemplary working radiographic workpiece guide in accordance with embodiments of the invention.

FIG. 3 shows an exemplary working radiographic workpiece guide 302. The working radiographic workpiece guide has a substantially flat or planar reference surface 304 that includes at least three non-collinear radioopaque fiducial markers 306, 308, 310. A pilot hole 318 marks the location (drill access) where drilling will take place to provide an implant shaft that receives, for example, the body of a dental implant fixture. The radiographic workpiece guide 302 also includes an alignment structure 320 located a predetermined distance "d" from pilot hole 318.

Figure 4:
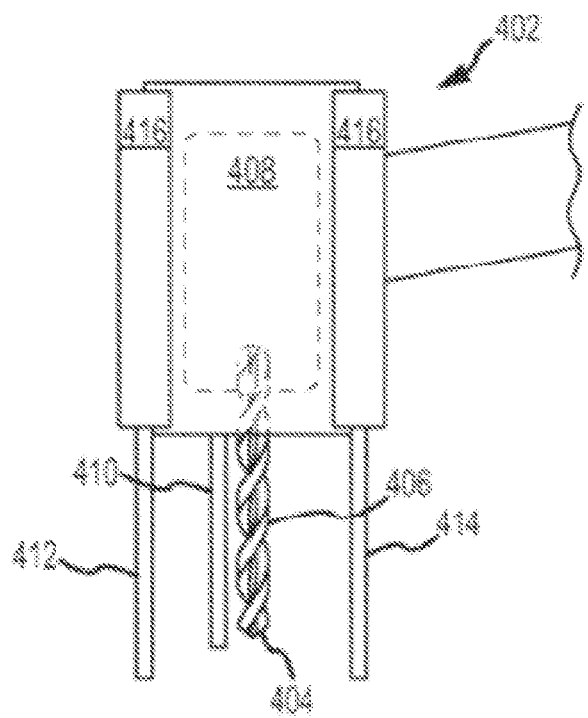
FIG. 4 shows an exemplary handpiece sensor assembly such as illustrated in FIGS. 1A-1C.

FIG. 4 shows an exemplary handpiece sensor assembly 402 including a drill tip 404, a drill shaft 406 attached to a dental drill engine 408, and at least three handpiece alignment sensors 410, 412, 414. The handpiece alignment sensors are generally linear and are formed from relatively inflexible material (i.e., metal, high impact plastic and the like). The sensors are each held within a sensor housing 416. Accordingly, the sensors are constrained to move only along the long axis thereof. The long axes of the handpiece alignment sensors are parallel to each other and parallel to the major axis of drill shaft 406. The handpiece alignment sensors are arranged about the major axis of drill shaft 406. The placement of the handpiece alignment sensors is not critical, provided that the tips of the handpiece alignment sensors are not collinear. In some embodiments, the handpiece alignment sensors are equidistant from the major axis of drill shaft 406, thus lying in a cylinder with a central axis coincident with the major axis of drill shaft 406. In some embodiments, the handpiece alignment sensors are evenly spaced about the cylinder. In some embodiments, the tip of each handpiece alignment sensors initially extends the same distance when not in use, such that the tips of the handpiece alignment sensors lie on a circle centered on and perpendicular to the major axis of drill shaft 406.

Figure 5:
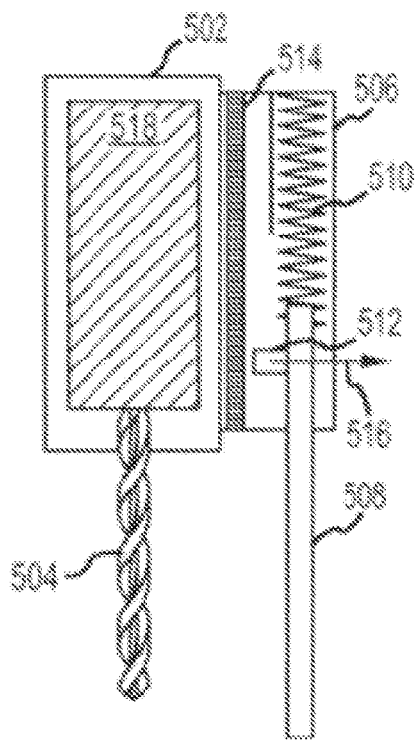
FIG. 5 shows the internal sensor structure of one sensor of a handpiece sensor assembly illustrated in FIG. 4.

FIG. 5 shows an exemplary handpiece sensor assembly (showing only one of the at least three alignment sensors and sensor housing thereof) including handpiece head 502, dental drill 504, dental drill engine 518, sensor housing 506, alignment sensor 508, spring 510, encoder optics 512, encoder ribbon 514 and encoder signal 516. Any suitable method is available for sensing of the position of the alignment sensor within the sensor housing. In some embodiments, the alignment sensor position is determined with encoder optics 512, which includes an LED/detector pair which senses the position along encoder ribbon 514, and transmits a signal via encoder signal 516 to the location system. For further example without limitation, in some embodiments, the encoder optics 512 are fixed with respect to the sensor housing, and the encoder ribbon 514 is affixed to alignment sensor 508.

The systems and methods described above may be implemented in a number of ways. One such implementation includes various electronic components. For example, units of the system illustrated in FIGS. 1A-1C may, individually or collectively, be implemented with one or more Application Specific Integrated Circuits (ASICs) adapted to perform some or all of the applicable functions in hardware. Alternatively, the functions may be performed by one or more other processing units (or cores), on one or more integrated circuits. In other embodiments, other types of integrated circuits may be used (e.g., Structured/Platform ASICs, Field Programmable Gate Arrays (FPGAs), and other Semi-Custom ICs), which may be programmed in any manner known in the art. The functions of each unit may also be implemented, in whole or in part, with instructions embodied in a memory, formatted to be executed by one or more general or application-specific processors.

Figure 6:
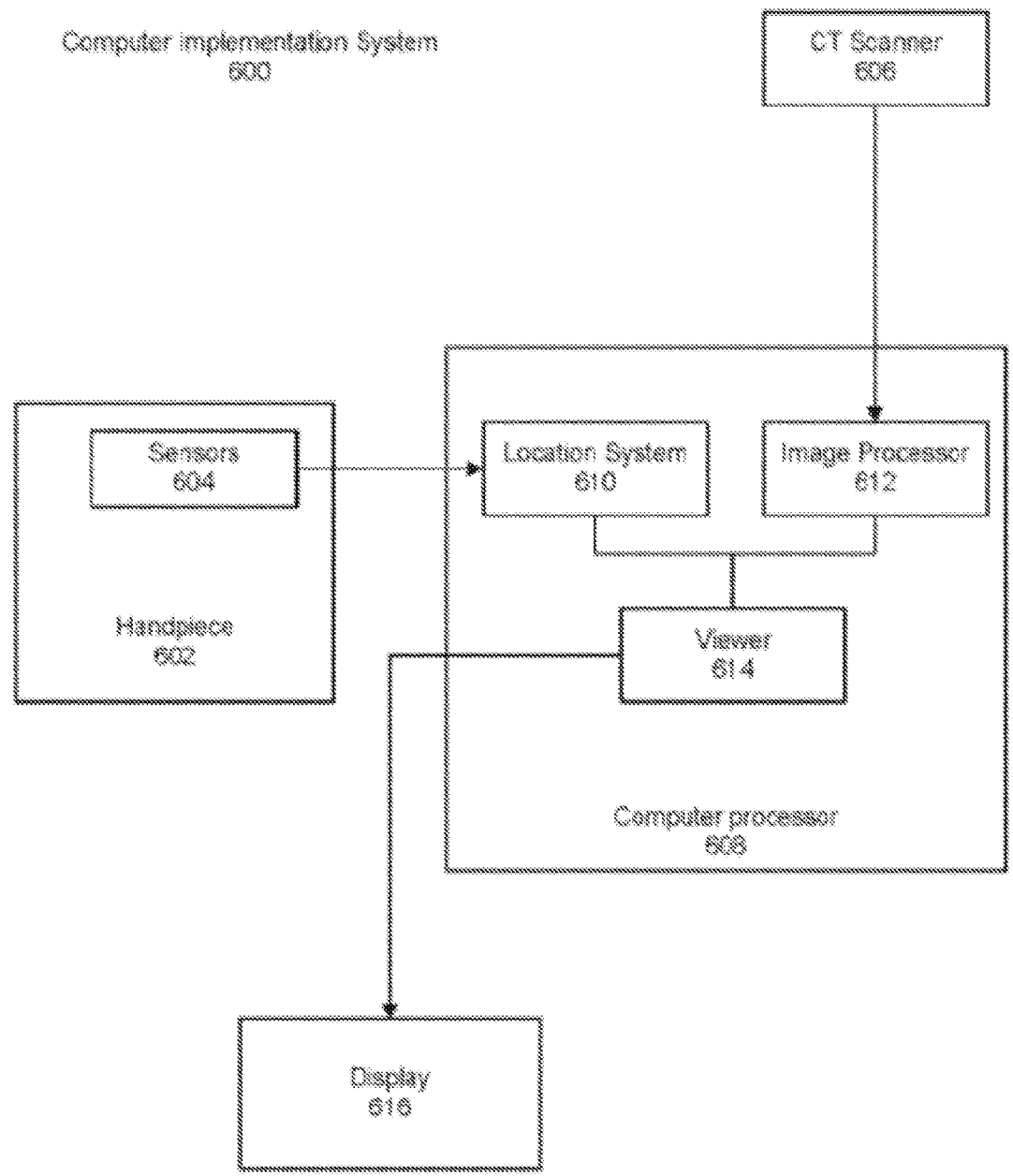
FIG. 6 shows a computer implementation system in accordance with embodiments of the invention.

FIG. 6 is a block diagram depiction of the computer implementation system 600 described herein, such as the system illustrated in FIGS. 1A-1C. The system components shown in FIG. 6 include a handpiece 602 that includes sensors 604. The sensors provide the depth and angular orientation information for performing the data manipulations described above. A CT scanner 606 provides the 3D x-ray image data comprising the guide situated at the worksite. The handpiece 602 and CT scanner 606 provide their respective data to a system processor 608. The system processor may comprise, for example, a desktop computer, workstation, laptop computer, or other computer platform with sufficient resources to perform the processing functions described herein.

The system processor 608 includes a location system 610 that receives the data from the handpiece sensors 604 and includes an image processor 612 that receives the data from the CT scanner 606. The location system 610 processes the sensor data, such as relative extension of the handpiece sensor probes, and performs computations to determine the angular orientation of the handpiece with respect to the top surface of the implant guide. The image processor 612 processes the CT scan data to produce image information for depiction of the implant guide on a display device along with the calculated position and orientation of the handpiece.

The system processor 608 also includes a viewer 614 that receives the depth and angular orientation information from the location system 610 and receives the image information from the image processor 612. In some embodiments, the viewer produces a viewing window that depicts the depth and angular orientation of the handpiece relative to the implant guide as a result of processing the location system information and the image processor information. The viewing window can be observed on a display device 616 that communicates with the system processor 608, such as a visual display device or a printer device. The location system 610, image processor 612, and viewer 614 may be implemented, for example, as application programs that are executed by the system processor 608, and may be implemented as a single application that incorporates all the functions of the three components 610, 612, 614 or any combination of other elements that provide equivalent processing.

Figure 7:
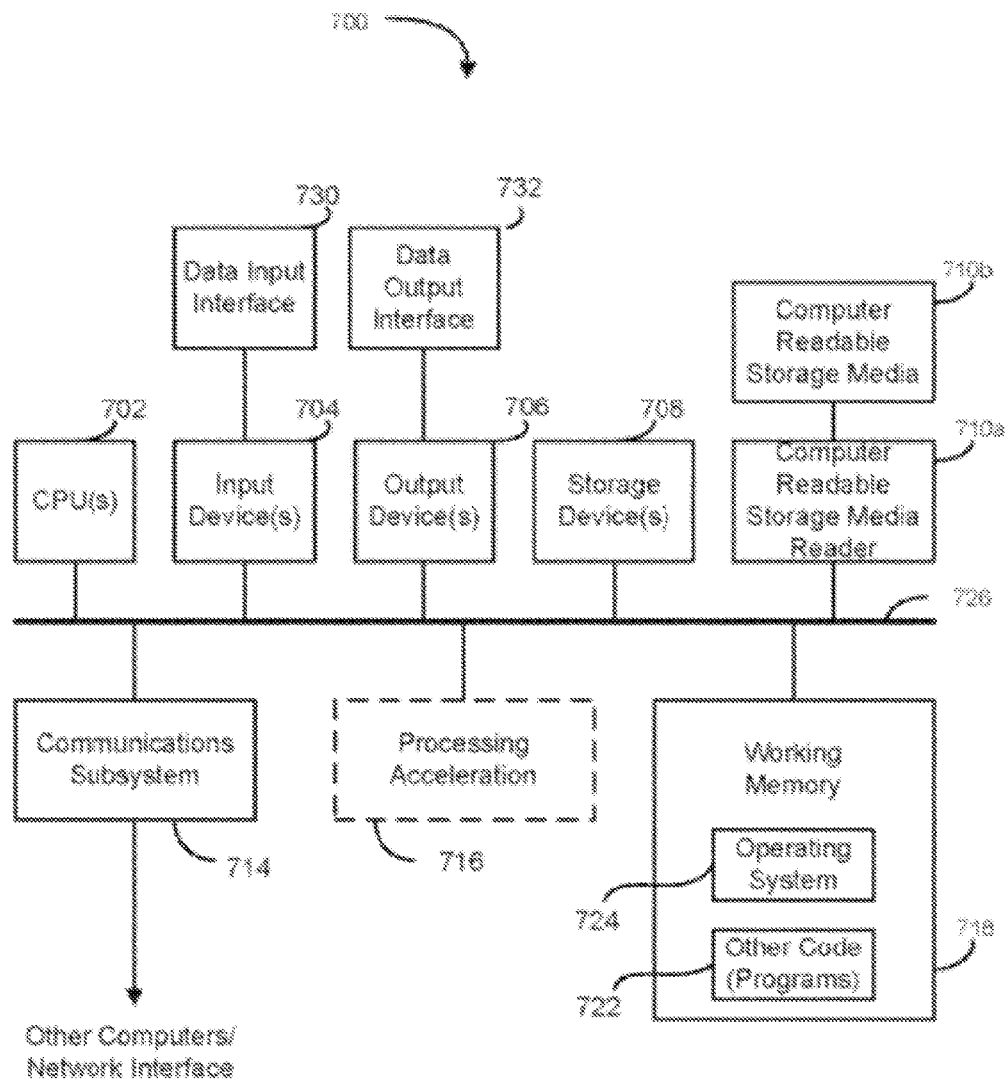
FIG. 7 shows a block diagram of an exemplary computer system in accordance with embodiments of the invention.

FIG. 7 is a block diagram of an exemplary computer system 700. In one embodiment, the computer system 700 may function as the system processor 608 shown in FIG. 6. It should be noted that FIG. 7 is meant only to provide a generalized illustration of various components, any or all of which may be utilized as appropriate. FIG. 7, therefore, broadly illustrates how individual system elements may be implemented in a relatively separated or relatively more integrated manner.

The computer system 700 is shown comprising hardware elements that can be electrically coupled via a bus 726 (or may otherwise be in communication, as appropriate). The hardware elements can include one or more central processor units (CPUs) 702, including without limitation one or more general-purpose processors and/or one or more special-purpose processors or processor cores. The hardware elements can further include one or more input devices 704, such as a computer mouse, a keyboard, a touchpad, and/or the like for providing user input to the CPU 702; and one or more output devices 706, such as a flat panel display device, a printer, visual projection unit, and/or the like.

The computer system 700 may further include (and/or be in communication with) one or more storage devices 708, which can comprise, without limitation, local and/or network accessible storage and/or can include, without limitation, a disk drive, a drive array, an optical storage device, solid-state storage device such as a random access memory ("RAM"), and/or a read-only memory ("ROM"), which can be programmable, flash-updateable, and/or the like.

The computer system 700 can also include a communications subsystem 714, which can include without limitation a modem, a network card (wireless or wired), an infra-red communication device, a wireless communication device and/or chipset (such as a Bluetooth device, an 802.11 device, a WiFi device, a WiMax device, cellular communication facilities, etc.), and/or the like. The communications subsystem 714 may permit data to be exchanged with other computers, with a network via a network interface, and/or any other external devices described herein. In many embodiments, the computer system 700 will further include a working memory 718, which can include RAM and/or ROM devices, as described above.

The computer system 700 also may include software elements, shown as being located within the working memory 718. The software elements can include an operating system 724 and/or other code, such as one or more application programs 722, which may comprise computer programs that are supported by the operating system for execution, and/or may be designed to implement methods described herein and/or configure systems as described herein. Merely by way of example, one or more procedures described with respect to the method(s) discussed above might be implemented as code and/or instructions executable by a computer (and/or a processor within a computer) such as the computer system 700. A set of these instructions and/or code might be stored on a computer readable storage medium 710*b*. In some embodiments, the computer readable storage medium 710*b* is the storage device(s) 708 described above. In other embodiments, the computer readable storage medium 710*b* might be incorporated within a computer system. In still other embodiments, the computer readable storage medium 710*b* might be separate from the computer system (i.e., it could be a removable medium, such as a compact disc, optical disc, flash memory, etc.), and or provided in an installation package, such that the storage medium can be used to program a general purpose computer with the instructions/code stored thereon. These instructions might take the form of executable code, which is executable by the computer system 700 and/or might take the form of source and/or installable code, which, upon compilation and/or installation on the computer system 700 (e.g., using any of a variety of generally available compilers, installation programs, compression/decompression utilities, etc.), then takes the form of executable code. In these embodiments, the computer readable storage medium 710b may be read by a computer readable storage media reader 710a of the computer system 700.

The various components of the computer system 700 communicate with each other via a system bus 726. Optional processing acceleration 716 may be included in the computer system, such as digital signal processing chips or cards, graphics acceleration chips or cards, and/or the like. Such processing acceleration may assist the CPU 702 in performing the functions described herein with respect to providing the display images.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

In some embodiments, one or more of the input devices 704 may be coupled with a data input interface 730. For example, the data input interface 730 may be configured to directly interface with the handpiece sensors 604 (see FIG. 6), whether physically, optically, electromagnetically, or the like. Further, in some embodiments, one or more of the output devices 706 may be coupled with data output interface 732. The data output interface 732 may be configured, for example, to produce data suitable for controlling tools or processes associated with the implant procedure, such as CAD/CAM systems or device manipulation and control systems.

In one embodiment, some or all of the display functions described herein are performed by the computer system 700 in response to the CPU 702 executing one or more sequences of one or more instructions (which might be incorporated into the operating system 724 and/or other code, such as an application program 722) contained in the working memory 718. Such instructions may be read into the working memory 718 from another machine-readable medium, such as one or more of the storage device(s) 708 (or 710). Merely by way of example, execution of the sequences of instructions contained in the working memory 718 might cause the processor(s) 702 to perform one or more procedures of the methods described herein.

The terms "machine readable medium" and "computer readable medium," as used herein, refer to any medium that participates in providing data that causes a machine to operate in a specific fashion. In an embodiment implemented using the computational system 700, various machine-readable media might be involved in providing instructions/code to processor(s) 702 for execution and/or might be used to store and/or carry such instructions/code (e.g., as signals). In many implementations, a computer readable medium is a physical and/or tangible storage medium. Such a medium may take many forms, including but not limited to, non-volatile media, volatile media, and transmission media. Non-volatile media includes, for example, optical or magnetic disks, such as the storage device(s) (708 or 710). Volatile media includes, without limitation, dynamic memory, such as the working memory 718. Transmission media includes coaxial cables, copper wire, and fiber optics, including the wires that comprise the bus 726, as well as the various components of the communication subsystem 714 (and/or the media by which the communications subsystem 714 provides communication with other devices). Hence, transmission media can also take the form of waves (including, without limitation, radio, acoustic, and/or light waves, such as those generated during radio-wave and infra-red data communications).

Common forms of physical and/or tangible computer readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, an EPROM, a FLASH-EPROM, any other memory chip or cartridge, a carrier wave as described hereinafter, or any other medium from which a computer can read instructions and/or code.

Various forms of machine-readable media may be involved in carrying one or more sequences of one or more instructions to the CPU 702 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computational system 700. These signals, which might be in the form of electromagnetic signals, acoustic signals, optical signals, and/or the like, are all examples of carrier waves on which instructions can be encoded, in accordance with various embodiments of the invention.

The communications subsystem 714 (and/or components thereof) generally will receive the signals, and the bus 726 then might carry the signals (and/or the data, instructions, etc. carried by the signals) to the working memory 718, from which the processor(s) 702 retrieves and executes the instructions. The instructions received by the working memory 718 may optionally be stored on a storage device 708 either before or after execution by the CPU 702.

The drilling of the implant shaft can be carried out with real-time update of the handpiece location and angular orientation with respect to the working guide and anatomical structures of the patient, free of viewing obstructions. The implantation process will next be described in greater detail.

Implantation Process

The sequence of events leading to the placement of a dental implant follows a path determined by the professional judgment and practice of the implant practitioner. A typical sequence is performed as follows:

Presentation. A patient in need of an implant would present for evaluation to a dental practitioner trained in the art of implantology (i.e., "an implant practitioner"). The terms "implantology" and the like refer in the customary sense to the practice of dentistry related to placing dental implants. Typically, the patient will have been referred by a general dentist, prosthodontist, restorative dentist, periodontist, or other practitioner as the result of a perceived need for an implant. A variety of needs for an implant are recognized in the art, including but not limited to replacing one or more teeth, providing an abutment to anchor a dental prosthesis, and in the extreme case of an edentulous patient, actually providing the sole anchoring means for a denture, bridge, or other dental prosthesis.

Evaluation. Patient evaluation determines whether a patient is a candidate for an implant. Evaluation considerations, in the professional judgment of the dental practitioner, include a variety of factors, including but not limited to, the general and oral health of the patient, medications currently taken by the patient, the site of the implant, proximity to adjacent teeth, and the positioning and morphology of adjacent anatomical landmarks including, but not limited to, the sinus and nasal passages and the floors thereof, other bony and nervous system features of the mandible or maxilla, the mental foramen, adjacent teeth, and available bone. The term "available bone" as used herein refers to tissue into which an implant may be placed. Available bone may include only naturally occurring bone, or may include additional material placed by a dentist to enhance the stability of an implant. A variety of methods for enhancing available bone are known in the art, including but not limited to, sinus lifting and bone grafting. Very high accuracy is required in dental implantology, where even a fraction of a millimeter of excess penetration, for example of the maxillary or mandibular tissue, or a small angular misalignment, for example 15, 10, 5, 4, 3, 2, or even 1 degree, can mean the difference between a successful and an unsuccessful procedure.

Patient evaluation can include acquiring and analyzing one or more conventional X-ray images (i.e., "screening X-rays"), as known in the art. Due to the limitations of 2-dimensional screening X-rays, the amount of available bone may not be known to the implant practitioner upon viewing only the screening X-rays. Those skilled in the art will know that multiple X-ray scans comprising a 3-dimensional radiographic scan, commonly referred to as a computerized axial tomography or computed tomography (CT scan), can provide a 3-dimensional view of anatomical structures. Accordingly, a 3-dimensional radiographic scan of the patient is desirable for at least the purpose of evaluation with respect to, for example, the amount of available bone.

Fabrication of initial radiographic workpiece guide. An initial radiographic workpiece guide having a construction similar to the workpiece guide 104 of FIG. 1B is fabricated for the patient. This process may include taking one or more impressions of the implant work area and adjacent teeth and other tissue including, but not limited to, the palate or portions thereof, forming a model based on the one or more impressions, and then fabricating the initial radiographic workpiece guide by methods known in the art. Additional methods for the fabrication of an initial radiographic workpiece guide are known in the art including, but not limited to, computer assisted manufacturing processes based on a previously obtained 3-dimension radiographic scan. The initial radiographic workpiece guide must be sufficiently sturdy to resist flexing under operation of the handpiece during dental surgery including implant placement.

3-dimensional imaging. A 3-dimensional radiographic scan (i.e., a "3-D scan" or "CT scan") is obtained of the patient while wearing the initial radiographic workpiece guide. In some embodiments, the 3-D scan provides a 3-dimensional computer representation of the patient's dentition, maxilla and/or mandible and associated dental structures by virtue of cross-sectional images spaced, for example, approximately 1 mm apart (i.e., 1 mm in image spacing), as known in the art. In some embodiments, the 3-D scan provides a user-controllable 3-dimension image on a display using computer graphic methods well-known in the art, for example but not limited to a mesh representation. The 3-D scan is stored in the system for later operation.

Figure 8A:
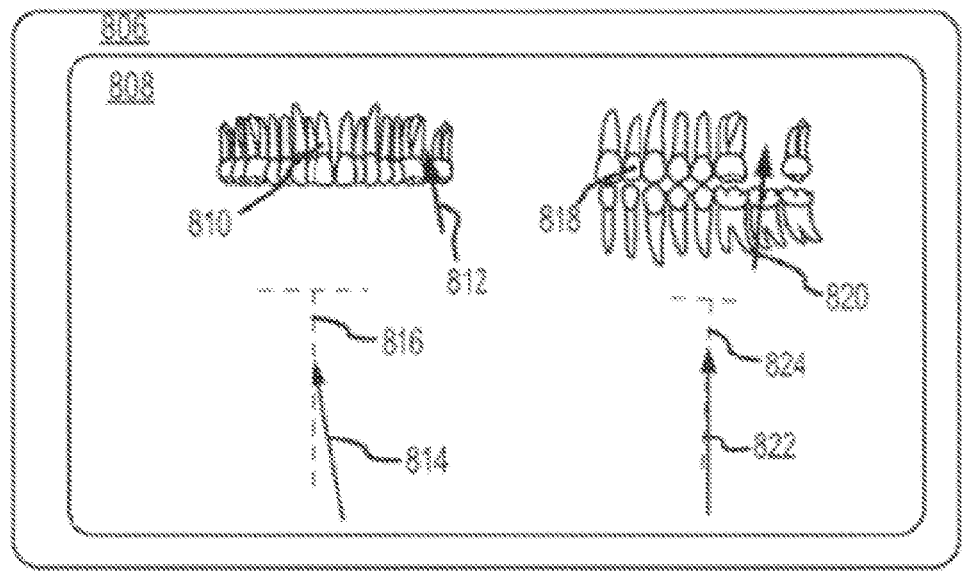
FIGS. 8A-8B show exemplary views of a CT scan of a patient as rendered on a display in accordance with embodiments of the invention. In both figures, an upper first adult molar is missing and is a candidate site for implantation.
Figure 8B:
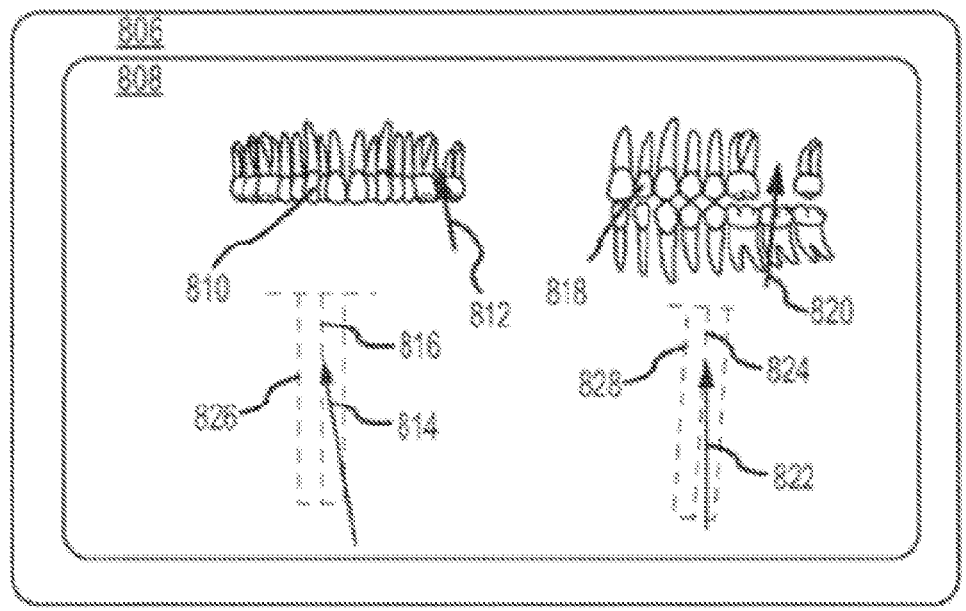

In FIGS. 8A-B, an exemplary CT radiographic scan is shown on display 808 of both figures, which display is connected to computer 806. In these figures, overlaid on the 3-D scan image representation at the implant site are shown drill position indicators 812 (right frontal view 810) and 820 (lateral view 818). The term "drill position indicator" refers to a display element which shows the real-time position of the drill. See e.g., display elements 814 and 822. The term "display element" refers in the customary sense to an object viewed on a display, including but not limited to 3-D scan image data representations, drill position indicators, position sprites, text, and the like. Conveniently, the drill position indicator can be distinguished from other display elements, for example without limitation, by color or texture coding, blinking, and the like. Additionally, drill position indicators 814 (frontal view) and 822 (lateral view) can be shown on display 808 to aid the implant practitioner during the drilling procedure. Regarding the position sprites which include display elements 814 and 816, and also 822 and 824, the dotted tee-shaped elements 816 and 824 represent the centerline of the desired implant shaft and furthest desired extent thereof, and the solid arrows 814 and 822 represent the drill position. The terms "position indicator," "position sprite," "sprite" and the like refer to a graphical representation of the position of the drill (e.g., 814 and 822) relative to the desired implant shaft in combination with a representation of the desired implant shaft and the maximum desired extent thereof (e.g., 816 and 824). In one embodiment illustrated in FIG. 8B, the desired bore size (width) of the desired implant shaft is additionally displayed, optionally with the centerline of the desired implant shaft. Merely for purposes of illustration, the position sprite including display elements 814 and 816 is shown in FIG. 8A, wherein the drill tip is on the centerline of the desired implant shaft, and the drill angle deviates from the desired angle. This representative orientation is reproduced in FIG. 8B. Similarly, the position sprite including display elements 822 and 824 shows the drill tip on the centerline of the desired implant shaft, and it further demonstrates a deviation from the desired angle. It is understood that multiple views of position sprites are useful in aligning the drill during boring, including for example, but not limited to, frontal and lateral views. Accordingly, the position sprite shown at the lower left of FIG. 8A corresponds to the drill position indicator for the frontal view shown on the left side of FIG. 8A, and the position sprite shown at the lower right of FIG. 8A corresponds to the drill position indicator for the lateral view shown on the right side of FIG. 8A. The relative orientation of display elements for FIG. 8A is reproduced in FIG. 8B, which further displays the desired bore size (width) of the desired implant shaft.

It is further understood that after registration of the handpiece, the position sprite can provide a real-time representation of the position of the drill relative to the implant site. In some embodiments, the drill position indicator is overlaid and displayed in registration with the 3-D scan image representation of the surrounding dental tissue. In some embodiments, one position sprite is overlaid and displayed in registration with the 3-D scan image representation of the surrounding dental tissue. In some embodiments, a plurality of 3-D scan image views, each overlaid with a position sprite, are displayed. In some embodiments, CT scan images are displayed. In some embodiments, a graphical representation of the position of the drill, including but not limited to depth and angular positioning, is displayed. In some embodiments, a plurality of position spites are displayed, each representing a different view (e.g., frontal, lateral and the like) of the implant site. See e.g., FIGS. 8A-B.

By viewing the 3-D scan, the implant practitioner judges whether the patient is a candidate for an implant, or whether the patient can become a candidate for an implant. In the event that the patient is not currently a candidate for an implant, due for example to insufficient available bone, the patient may become a candidate for a procedure to enhance the available bone, as described herein and/or as known in the art. If the patient successfully responds to treatment to enhance the amount of available bone, then the patient can be re-evaluated for implant placement.

Figure 9:
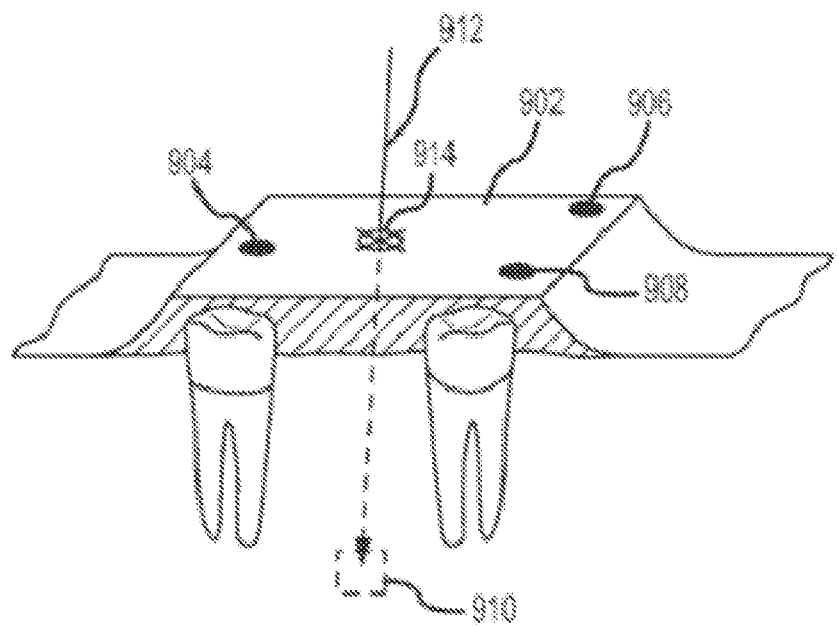
FIG. 9 shows an exemplary radiographic workpiece guide in place adjacent to an implant work site. Legend: base (i.e., furthest extent) of proposed implant fixture (box); proposed implant path (solid arrow); intersection of proposed implant path and planar reference surface of the radiographic workpiece guide (open circle with sight reticule).
Figure 10:
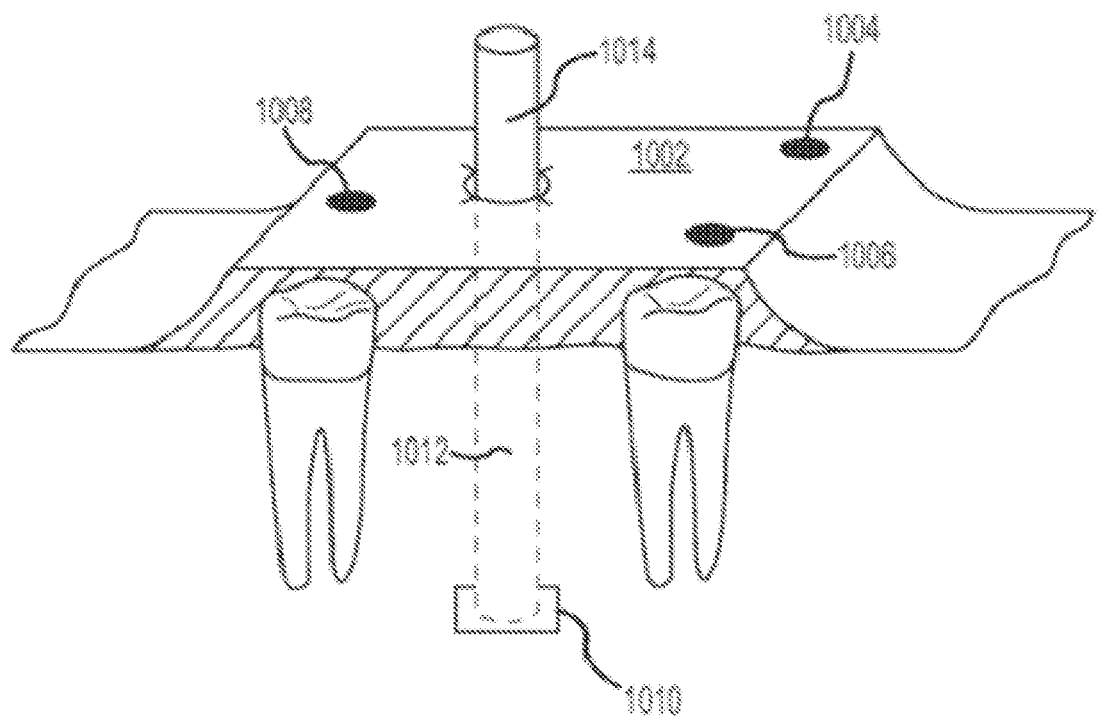
FIG. 10 is an exemplary schematic drawing corresponding to the view shown in FIG. 9. The implant shaft which will accommodate the implant fixture is shown as a cylinder. The intersection of the centerline of the cylinder with the planar reference surface determines the location of the pilot hole.

Determining implant location and implant shaft orientation. If the patient is a candidate for an implant, the desired location for the implant is determined by viewing the 3-D scan, taking into consideration the aesthetics and mechanical stability of the proposed implant placement The position and angle of the contemplated implant shaft corresponding to the desired implant location is identified by the practitioner and is stored in the location system. The practitioner can use a graphical user interface program of the system to view the 3-D scan and designate the desired implant location. In some embodiments, the position and angle of the desired implant shaft is determined by interactive 3-dimensional viewing of the 3-D scan through a software system of the processor. An exemplary display afforded to the implant practitioner is shown in FIG. 9. In this figure, a working radiographic guide having a planar reference surface 902 is affixed in the patient's mouth. In the figure, the patient is missing a tooth which will be replaced with an implant and pontic attached thereto. Radioopaque fiducial markers 904, 906 and 908 are displayed in the figure. The furthest extent of the desired implant shaft to be drilled to accommodate an implant fixture is indicated with an open box (910). An arrow 912 indicating the path to be drilled for the implant shaft and subsequently used to insert the implant fixture is displayed. The intersection of the implant shaft path arrow 912 with the planar reference surface 902, at which position a pilot hole 914 will be drilled in the planar reference surface 902 to provide drill access, is indicated by an open circle overlaid with a sight reticule. Shown in the schematic diagram of FIG. 10, the planar reference surface 1002 lies above the missing tooth (FIG. 9). Radioopaque fiducial markers 1004, 1006 and 1008 define the plane of the planar reference surface. The furthest extent of the implant shaft 1010 defines the position of one end of a cylinder 1012 which corresponds to the implant shaft drilled to accommodate the implant fixture (i.e., arrow 912). The intersection of the centerline of the cylinder 1012 with the planar reference surface 1002 defines the position of the pilot hole 1014, indicated by an open circle overlaid with a sight reticule. A variety of interactive graphical methods are available to manipulate the arrow 912, or equivalently the cylinder 1012. For example, different views (e.g., frontal, left lateral, right lateral, and the like) can be simultaneously displayed, optionally displaying the results of the CT scan superimposed with the current position of the arrow 912 or cylinder 1012. The different views can be displayed orthogonally (i.e., rotated 90-deg about one or more axes). In some embodiments, the different views are not displayed orthogonally. In some embodiments, the display of FIG. 9 is manipulated in 3-dimensional space (i.e., as viewed on the display), depending on the preference of the implant practitioner, allowing refinement of the position of the arrow 912 or cylinder 1012 by rotation of the display. Methods for manipulation of 3-dimensional displays (e.g., rotation, translation, scaling and the like) of images and overlaid structures representing desired implant shaft orientation and the like, are well known in the art. When a suitable positioning of the implant shaft, and hence pilot hole 914 or 1014, is determined, the implant practitioner provides a signal to the computer system which then stores the position and orientation data. The location of the implant shaft may be correlated with features of the radiographic workpiece guide, for example the fiducial markers, and the correlation stored for use in future steps in the process.

Accordingly, the system can determine the location and orientation of the implant shaft centerline from the designated implant location. Positional information relating to the intersection of the implant shaft centerline with the drill reference surface is calculated and stored in the location system, and additionally can be provided to the implant practitioner. The position of at least one alignment structure at the drill reference surface is calculated by the location system from the location data relating to the implant shaft centerline and top surface, and can be provided to the implant practitioner.

Figure 11:
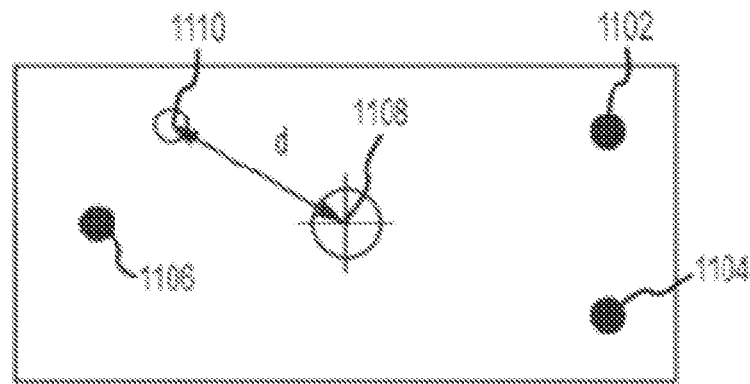
FIG. 11 shows an exemplary mask which provides location information for a pilot hole and at least one alignment structure. Legend: radioopaque fiducial markers (open circle); pilot hole location (open circle with sight reticule); alignment structure (closed circle).

Preparing for registration. With positional information available relating to the intersection of the implant shaft centerline with the drill reference surface, a pilot hole is drilled in the radiographic guide to mark the axial centerline of the implant shaft on the drill reference surface. The pilot hole should have a diameter that is sufficiently small to receive the drill tip of a handpiece drill and be centered without free play within a desired error tolerance. Regarding the desired error tolerance, for a 2 mm drill tip, the error tolerance in placement of the pilot hole can be 0.5 mm, 0.4 mm, 0.3 mm, 0.2 mm 0.1 mm or even less. Corresponding error tolerances can be calculated for different diameter drill tips, as known in the art. In some embodiments, the position of the pilot hole is printed on a transparent or semi-transparent mask. The mask reproduces the drill reference surface at physical scale (i.e., 1:1 representation), showing the fiducial markers and the location of the pilot hole and at least one alignment structure. Conveniently, the mask can be temporarily affixed atop the drill reference surface, which can then be marked (e.g., through the mask with a sharp implement) to show the location of the pilot hole and the at least one alignment structure. The pilot hole can then be opened by e.g., drilling, either in the patient's mouth or outside of the mouth. In a preferred embodiment, the pilot hole is opened by drilling outside of the mouth. An exemplary mask useful for marking the pilot hole and alignment structure locations is shown in FIG. 11. FIG. 11 includes indicia for the radioopaque fiducial markers 1102, 1104 and 1106, shown as closed circles in the figures. The site of the pilot hole 1108 is indicated by an open circle with an overlaid sight reticule. The position of the at least one alignment structure 1110 is indicated by an open circle. The distance "d" between 1108 and 1110 is known. Preferably, the distance d is chosen to be equal to the distance between the centerlines of the handpiece drill and at last one sensor. In some embodiments, an additional alignment structure is provided such that each of two alignment sensors can be received into each of two alignment structures.

Additionally, at least one alignment structure is formed in the drill reference surface. The at least one alignment structure is a fixed and known distance from the centerline of the implant shaft and from the center of the pilot hole. The alignment structure may comprise, for example, a detent or depression in the drill reference surface such that the tip of one of the handpiece sensors engages the detent or depression. That is, the tip of one of the handpiece sensors is easily received into the detent and thereby provides the implant practitioner with mechanical feedback to verify that the handpiece is in the proper location whenever the handpiece is positioned within the patient's mouth. The distance between the alignment structure and the pilot hole center is conveniently the radial distance between the axial centerlines of the drill shaft and at last one alignment sensor in the handpiece-sensor assembly. In some embodiments, one of the radioopaque fiducial markers serves the role of providing the location for an alignment structure.

Figure 12:
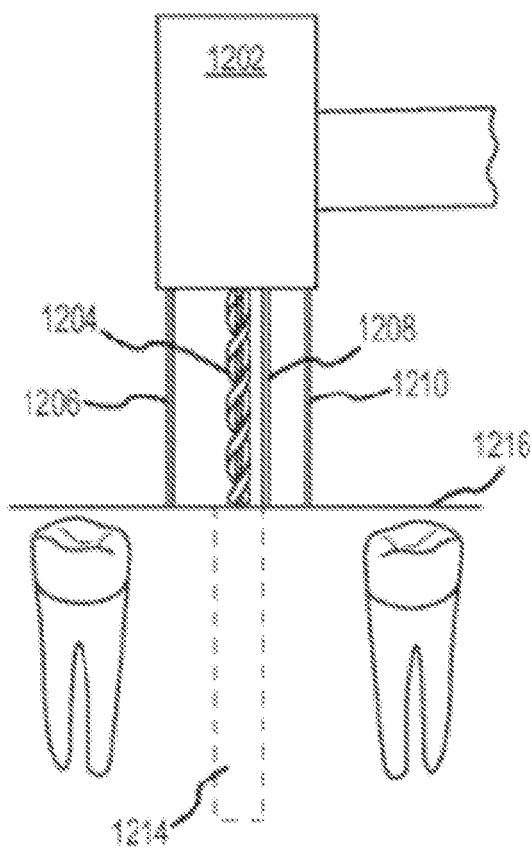
FIG. 12 shows the relative positioning of the handpiece sensor assembly with the implant worksite after registration but prior to drilling into the dental tissue. The proposed implant shaft (1214) is shown. Left panel: lateral view; right panel: frontal view.

Registration of the handpiece. Once the 3-D scan data is stored into the system processor (computer) along with information on the configuration of the handpiece-sensor assembly, such as sensor and drill shaft spacing, the handpiece is said to be registered to the system. At this point, in some embodiments the pilot hole may be enlarger to provide the drill access. The location of the handpiece is known to the location system because the handpiece drill bit is centered within the pilot hole and at least one sensor of the handpiece head is centered within an alignment structure. Upon registration, the system provides a display showing the actual real-time position and orientation of the handpiece relative to the radiographic workpiece guide and the desired implant shaft. For example, the actual position and orientation of the handpiece head can be indicated by a solid line on the display and the desired position and orientation of the handpiece head can be indicated by a dashed line on the display. A perspective view can be shown or, for example, frontal and lateral views can be provided on the display. An exemplary display showing the initial position of the drill relative to the implant worksite is shown in FIG. 12. Further regarding this figure, the handpiece sensor assembly 1202, including drill 1204 and sensors 1206, 1208 and 1210, is positioned above the desired implant shaft 1214. The tip of drill 1204 sits at the pilot hole 1212 corresponding to the centerline of desired implant shaft 1214 (not shown). Each of the sensors is in contact with the planar reference surface 1216. The depth of drilling is initially zero; i.e., the drill tip is positioned at the pilot hole. As the drill moves through the drill access, the sensors compress, and the updated positional information is provided to the location system.

In one embodiment, the handpiece registration process can include the operations of: (a) contacting a handpiece alignment sensor with an alignment structure of the initial radiographic workpiece guide while ensuring that at least two other handpiece alignment sensors make contact with the drill reference surface and at least one of the alignment sensors is not at full extension; (b) centering a handpiece drill tip at the pilot hole; and (c) providing a registration signal to the processing system operationally connected to the handpiece-sensor assembly, thereby providing the current angular and positional location of the handpiece head with respect to the radiographic workpiece guide and providing a registered handpiece. The registration signal may be produced, for example, by pressing or articulating an alignment sensor against full extension, or by clicking a display button, or pressing a physical registration switch or button, or the like.

Alternatively, the handpiece registration process can include the operations of: (a) articulating an alignment structure of the initial radiographic workpiece guide with a handpiece alignment sensor while ensuring that at least two other handpiece alignment sensors articulate the drill reference surface; (b) visually aligning the drill tip to a position which approximates the position of the pilot hole; and (c) providing a registration signal to the processing system operationally connected to the handpiece-sensor assembly, thereby providing the current angular and positional location of the handpiece head with respect to the radiographic workpiece guide and providing a registered handpiece. The registration signal may be provided as noted above.

Figure 13:
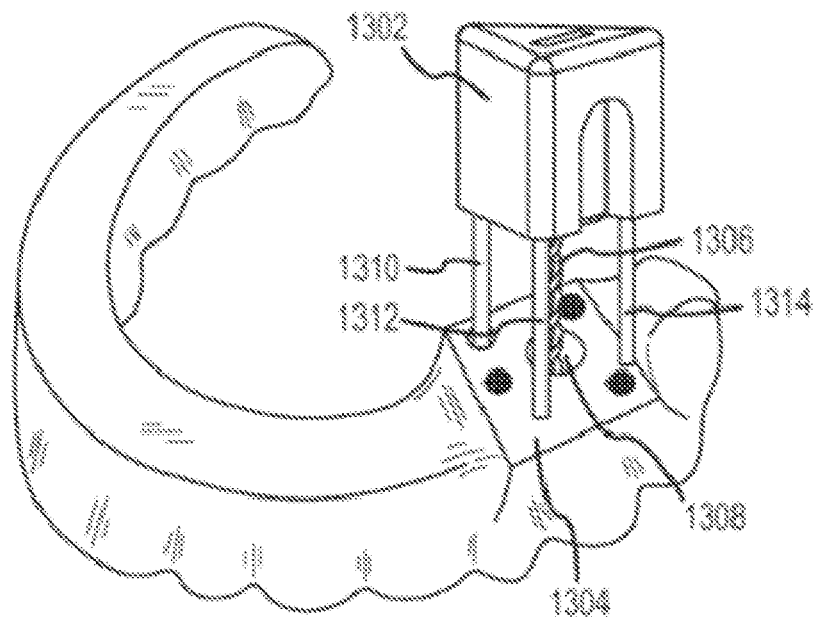
FIG. 13 shows a handpiece sensor assembly 1302 positioned above the planar reference surface 1304. The drill 1306 is positioned at the pilot hole 1308. At least one sensor (1310, 1312, 1314) is positioned at an alignment structure (not shown) on the planar reference surface.

After registration, the system can thereafter determine in real time the position of the handpiece relative to the radiographic fiducial marks by the system processor receiving extension information from each of the handpiece alignment sensors. That is, the amount of extension for each sensor relative to the handpiece is known, so that the location of the sensor end is known, as is the location of the drill tip relative to the handpiece head. In this way, the extension information determines the relative angle between the axis of the handpiece head and the drill reference surface. In some embodiments, registration occurs with the initial radiographic workpiece guide in place in the mouth. In some embodiments, registration occurs with the initial radiographic workpiece guide outside of the mouth, in which case the workpiece guide is re-inserted into the mouth prior to drilling. As shown in FIG. 13, the handpiece sensor assembly 1302 is positioned above the planar reference surface 1304. The drill 1306 is positioned at the pilot hole 1308. At least one sensor (1310, 1312, 1314) is positioned at an alignment structure (not shown) on the planar reference surface. In FIG. 13, the radioopaque fiducial markers are shown as unlabeled closed circles.

Post-registration steps. After registration, the pilot hole can be conveniently enlarged by using a handpiece drill at the pilot hole to afford the drill access. Typically the drill access is enlarged only to the extent necessary to accommodate the drill tip, drill shaft, and optional drill shaft extension, and additional area for irrigation and aspiration. In some embodiments, the pilot hole is enlarged to form the drill access while the radiographic workpiece guide is outside of the mouth of the patient. The radiographic workpiece guide is subsequently re-inserted prior to drilling the implant shaft.

Real-time display of the drilling. After handpiece registration is completed, the location system combines the 3-D scan data from the patient images with the extension information from the handpiece sensors. The system knows the location of the drill reference surface of the working radiographic workpiece guide from the at least three radioopaque markers in the 3-D scan data. The system knows the location of the handpiece relative to the alignment structure of the radiographic workpiece guide from the registration process. The system knows the spatial relationship of the workpiece guide with respect to the patient's dentition from the 3-D scan data and the fact that the workpiece guide is affixed to the dental arch of the patient. The system knows the angle and depth of the handpiece drill tip relative to the working radiographic workpiece guide from the handpiece sensor extension information. The system knows the desired location and angle of the implant shaft relative to the working radiographic workpiece guide from the determination of implant location and implant shaft orientation as described above. From all this information, a software application of the location system combines all the data and produces information for display of a 3-dimensional image with real-time update of the handpiece location relative to the desired location and angle of the implant shaft.

In some embodiments, a software application of the location system combines the location and orientation data for the handpiece, planar reference surface, desired implant shaft and furthest extent thereof, and provides information to the implant practitioner with real-time update of the handpiece location relative to the desired location and angle of the implant shaft. In some embodiments, the software application additionally calculates the location and/or orientation of the drill relative to the desired implant shaft, the desired furthest extent of the implant shaft or other dental structures in the implant site including, but not limited to, available bone positioning, adjacent teeth and/or root, and the like. In some embodiments, a warning is issued to the implant practitioner if the drill angle deviates beyond a pre-set threshold from the desired implant shaft orientation, as the drill tip approaches the desired furthest extent of the implant shaft, or as the drill tip approaches a dental structure within the implant site. In some embodiments, the warning information is provided in the form of a visual cue on the display. The visual cue may be displayed in addition to other displayed information, for example but not limited to, drill position indicator, position sprites, text, and the like. Exemplary visual cues include, but are not limited to, presentation of a color display element, flashing display element and the like, as known in the art. In some embodiments, the warning information is additionally provided in the form of a sound cue. Exemplary sound cues include, but are not limited to, a tone, a bell or other warning sound as known in the art, a voice and the like. In some embodiments, the voice is pre-recorded. In some embodiments, the voice is generated by computer methods well known in the art. Exemplary sound cues using a voice include, but are not limited to, status statements (e.g., "2 millimeters remaining" and the like to indicate remaining depth to be drilled) or warning statements (e.g., "WARNING: approaching margin" and the like).

Prior to drilling into available bone, the implant practitioner may temporarily move gingival tissue by, for example without limitation, incising to form a flap as known in the art. The gingival tissue may be removed with, for example, a tissue biopsy punch.

Figure 14:
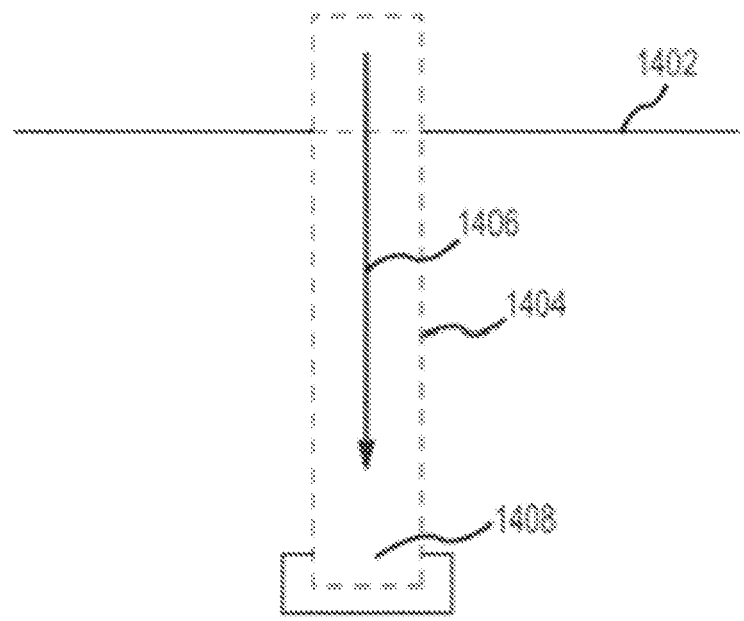
FIG. 14 shows an exemplary real-time display of the implant work site, showing the gingival surface 1402, the desired implant shaft 1404, the current real-time position of the drill 1406, and the desired furthest extent of the implant shaft 1408.

FIG. 14 provides another exemplary display during boring of the implant shaft. The gingival surface 1402 is indicated. A graphical representation display element of the desired implant shaft 1404 is fixed with respect to the surround tissue and gingival surface. The real-time position of the drill is indicated by arrow 1406, as it moves along and about display element 1404. The furthest extent of the implant shaft 1408 is indicated at the end of display element 1404. In some embodiments, components 1402, 1404, 1406 and 1408 of the display are color coded, texture coded, and/or displayed in a variety of styles available to one skilled in the art. In some embodiments, the positional information is provided in a position sprite representation, as described herein. In some embodiments, position and angular information is displayed as textual information. In some embodiments, the computer system records the position and angular information as a function of time during the implant drilling procedure.

It should be apparent that the presentation of location information as described herein does not require a visual image of the work site (i.e., patient's mouth). The implant practitioner can thereby use the real-time 3-dimensional presentation of the system as the sole source of information to guide the drilling process. As the drill bit augers into the bone material, the location system receives information on the changing (decreasing) sensor extension and updates the presentation accordingly. That is, the location system will determine the depth of the drill bit into the available bone based on the updated real-time information about the sensor extensions and will update the presentation display to show the changing depth of the drill bit. In some embodiments, drilling can proceed without the implant practitioner needing to view the actual implant worksite. Conveniently, the 3-D scan image and real-time positional information for the drill are impervious to local tissues and fluids (blood and irrigating water) at the drilling site. If desired, the display presentation can combine viewable (optical) images to provide a "virtual reality" presentation for the implant practitioner. The viewable images can comprise pre-existing imagery, current imagery, or computer-generated imagery.

In some embodiments, the handpiece is not re-registered when the handpiece is withdrawn from the mouth, for example, to change drill bits. In some embodiments, each time the handpiece is withdrawn from the patient, such as to change to a different drill bit, the handpiece can be re-registered so its location relative to the working radiographic workpiece guide and alignment structures is again known to the location system. In some embodiments, upon installing a larger drill, the system is registered by positioning the larger drill tip at the gingival or available bone surface and providing a signal to the location system. The real-time updates to the 3-dimensional images can then be produced, optionally after re-registration, and the drilling operation can continue with the updated display presentation. Alternatively, in some embodiments the handpiece need not be re-registered, as the geometrical information on a newly placed handpiece drill can be provided to the processing system, and appropriate corrections to the position of the handpiece drill can be calculated and displayed.

Figure 15:
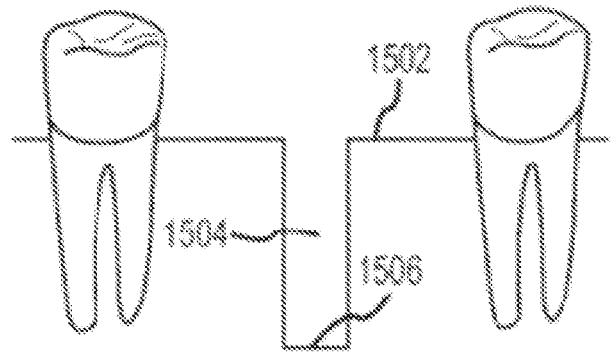
FIG. 15 shows a display of the implant work site at the conclusion of the implant shaft drilling procedure. An implant shaft 1504 has been bored through the gingival surface 1502 to the desired depth 1506.

As shown in FIG. 15, at the conclusion of the implant shaft drilling procedure, the handpiece assembly is withdrawn from the patient's mouth. There remains an implant shaft 1504, bored through the gingival surface 1502 to the desired depth 1506. At this point, the radiographic guide can be withdrawn from the mouth, and the implant fixture can be seated.

Workpiece Guide with Displaced Drill Reference Surface

Figure 16:
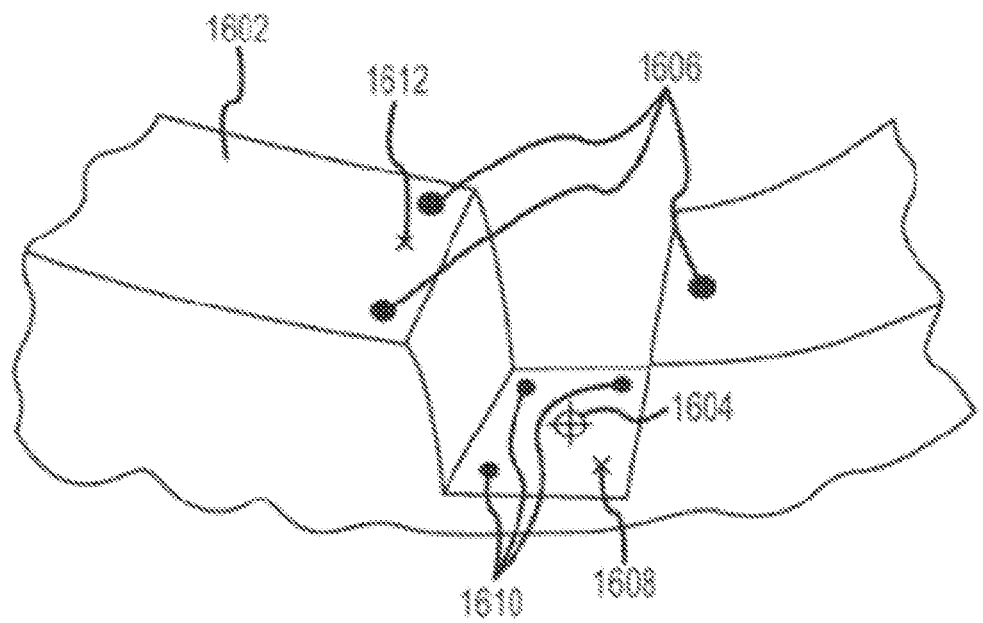
FIG. 16 shows a radiographic guide 1602 in which the pilot hole 1604 lies in a different plane than that defined by radioopaque fiducial markers 1606.

In an alternative embodiment, there is provided a radiographic workpiece guide with a planar reference surface that is displaced from the top surface of the guide. Such a construction is illustrated in FIG. 16, which includes radiographic workpiece guide 1602, pilot hole 1604, radioopaque fiducial markers 1606, alignment structure 1608, and optional secondary radioopaque fiducial markers 1610. Optionally, an alignment structure 1612 is present in the plane defined by markers 1606. In FIG. 16, it should be apparent that the at least three fiducial markers 1606 that define the top surface of the radiographic workpiece guide are in a different plane from that of the drill reference surface containing the pilot hole 1604 and the alignment structure 1608. In some embodiments having radioopaque fiducial markers 1610, the location system keeps track of the planes separately defined by fiducial markers 1606 and 1610. In some embodiments, the sensors of the handpiece sensor assembly articulate the plane defined by fiducial markers 1606. In some embodiments, the sensors of the handpiece sensor assembly articulate the plane defined by fiducial markers 1610. In some embodiments, at least one of the sensors articulates alignment structure 1608. In some embodiments, at least one of the sensors articulates alignment structure 1612.

Non-Medical Device and Method

In another aspect, there is provided a plurality of alignment sensors within a drill alignment sensor sub-assembly which can be removably attached to a drill. A drill configured with the alignment sensor sub-assembly is suitable for a non-medical use. The drill for a non-medical use includes a drill engine and associated housing, a chuck attached thereto, and a drill bit held by the chuck, as conventionally known in the art. The drill bit includes a drill body and a drill tip, as conventionally known in the art. The plurality of alignment sensors are connected to a computer system that includes a location system that receives information on the extension of the alignment sensors. The computer system further includes a display that provides real-time information on the depth and orientation of the drill bit relative to the surface articulated by the alignment sensors. The computer system can further optionally include circuitry for user input, for example without limitation, power, reset and user operational inputs. The computer system, including but not limited to location system, display, power source, associated circuitry and the like, can be fabricated using components and designs well known in the art and described herein. The term "drill alignment sensor sub-assembly" refers to a sub-assembly including a plurality of alignment sensors which can be attached to a drill for a non-medical use. The term "drill for a non-medical use" refers to a drill useful for drilling in a non-medical or non-dental application, for example, but not limited to, accurately drilling a hole into a non-medical workpiece. The terms "non-medical workpiece" and the like refer to a solid material such as, for example, wood, metal, plastic and the like, which material can be drilled. Preferably, the non-medical workpiece includes a substantially planar surface into which the drill for a non-medical use will bore, which substantially planar surface can accommodate the tips of the alignment sensors during drilling. In some embodiments, extension information from one or more of the plurality of alignment sensors is ignored during drilling. Information on which alignment sensors to use (or ignore) can be provided, for example, by the user operational input circuitry.

Figure 17:
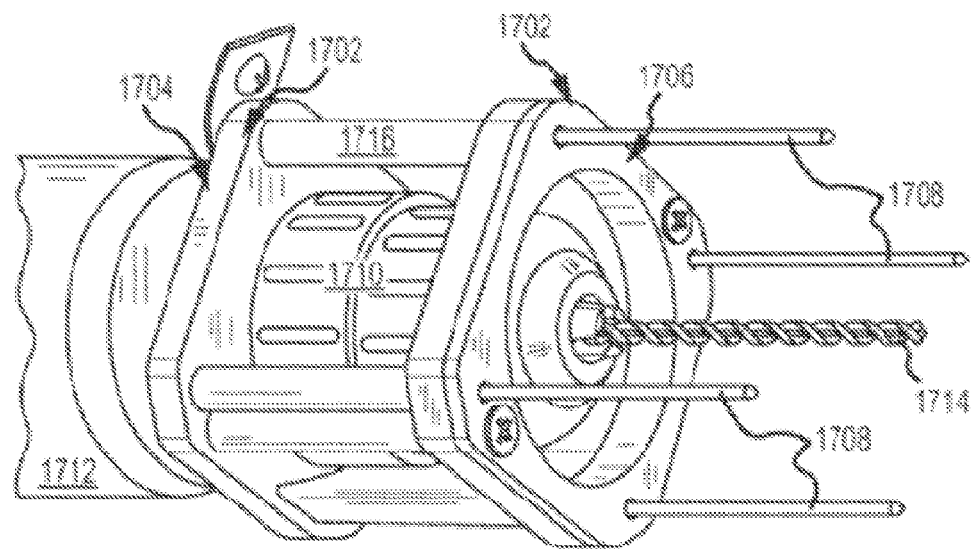
FIG. 17 shows a drill alignment sensor sub-assembly attached to a drill for a non-medical use, as described herein.

A representative drill alignment sensor sub-assembly is shown in FIG. 17. In the figure, drill alignment sensor sub-assembly 1702 is shown attached to a commercially available standard hand drill 1712 having a drill bit 1714 held by a chuck 1710. The drill alignment sensor sub-assembly 1702 includes supporting structures 1704 and 1706. Connecting supporting structures 1704 and 1706 are alignment sensor housings 1716 as described herein. See e.g., FIG. 5. Projecting from sensor housings 1716 are alignment sensors 1708. The drill alignment sensor sub-assembly 1702 is mounted such that alignment sensors 1708 are collinear with, and distributed about, drill bit 1714. Support structures 1704 and 1706 and/or alignment sensor housings 1716 include position sensing devices as described herein to determine the position (i.e., extension) of each alignment sensor 1708. See e.g., FIG. 5. The positions of alignment sensors 1708 are provided to a computer system which can then display in real-time positional information (e.g., angle and depth) of drill bit 1714 relative to the non-medical workpiece which alignment sensors 1708 articulate, by computational methods known in the art.

In some embodiments, the drill alignment sensor sub-assembly is conveniently combined with the computer system into a single unit. A variety of configurations are available, in each of which the computer system can receive information about the orientation and depth of the drill bit and provide orientation and depth information on a display. In some embodiments, the combination of the drill alignment sensor sub-assembly and the computer system is removably attachable to a drill for a non-medical use. In some embodiments, the combination of the drill alignment sensor sub-assembly and the computer system is permanently affixed to a drill for a non-medical use.

In yet another aspect, there is provided a method for accurately drilling a hole (i.e., with respect to, for example, orientation angle and depth) using a drill for a non-medical use in combination with a drill alignment sensor sub-assembly and a computer system connected to, and capable of receiving information from, the alignment sensors of the drill alignment sensor sub-assembly. The drill alignment sensor sub-assembly is affixed to a drill. See e.g., FIG. 17. The alignment sensors are initially positioned on the non-medical workpiece, and the drill bit is positioned above the desired hole. As the drill for a non-medical use bears down on the workpiece, the positions of the alignment sensors change. The real time position of the alignment sensors is received by the computer system which calculates the angle and depth of the drill bit by methods well known in the art. This information is then provided on a display. In some embodiments, angular and depth information is provided. In some embodiments, a visual depiction of the orientation and depth of the drill bit relative to the non-medical workpiece is provided. In some embodiments, the computer system can receive a signal to ignore the extension information from one or more of the plurality of alignment sensors. Preferably, the information from at least three alignment sensors is used in the calculation of the positional information (e.g., angular orientation and drill bit depth).

Handpiece Attachment

In another aspect, the sensors may be included in an attachment that is configured to attach to an existing dental handpiece. In this way, an existing dental handpiece may be retrofitted for use in embodiments of the invention.

Figure 18:
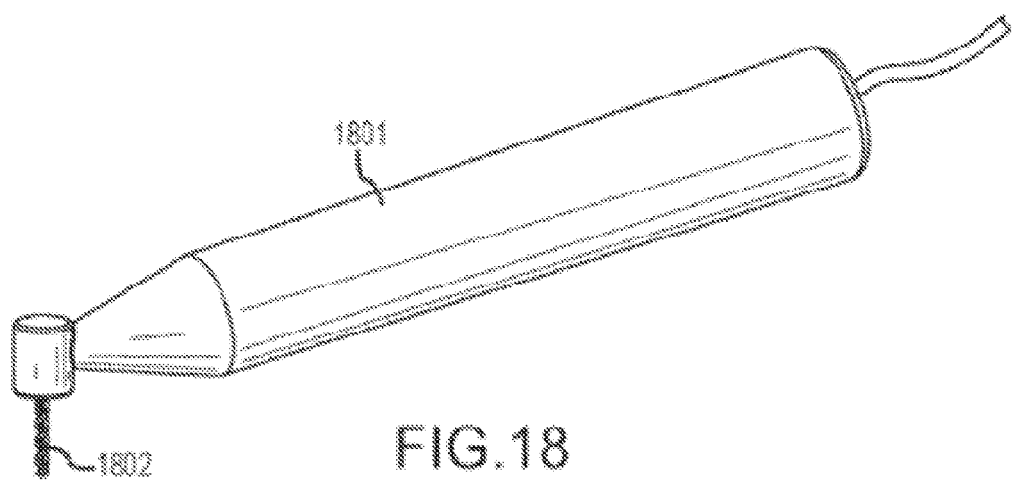
FIG. 18 illustrates a typical dental handpiece suitable for use in embodiments, including a drill bit.

FIG. 18 illustrates a typical dental handpiece 1801 suitable for use in embodiments, including a drill bit 1802. While drill bit 1802 is shown as a twist drill, it will be understood that embodiments of the invention may utilize other kinds of drill bits. Dental handpiece 1801 may include a motor, for example a pneumatic motor capable of rotating drill bit 1802 at a rotational speed recommended by the dental implant manufacturer or as known in the art. Exemplary rotational speeds in this context can be from about 800-1500 rpm (revolutions per minute), e.g., about 800, 900, 1000, 1100, 1200, 1250, 1300, 1400 or 1500 rpm. As shown, dental handpiece 1801 does not provide feedback as to its position or angular orientation in relation to the work site.

Figure 19A:
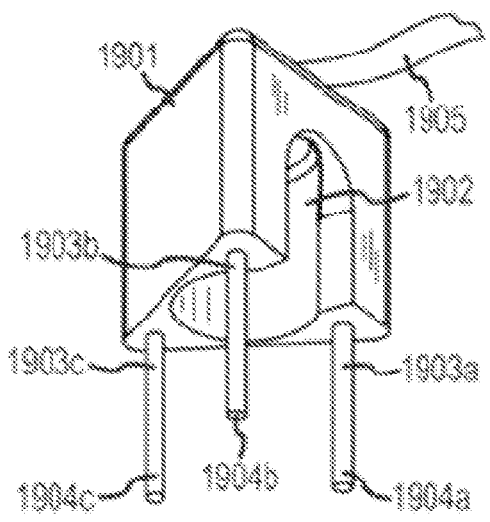
FIG. 19A illustrates an oblique view of an attachment in accordance with embodiments of the invention.
Figure 19B:
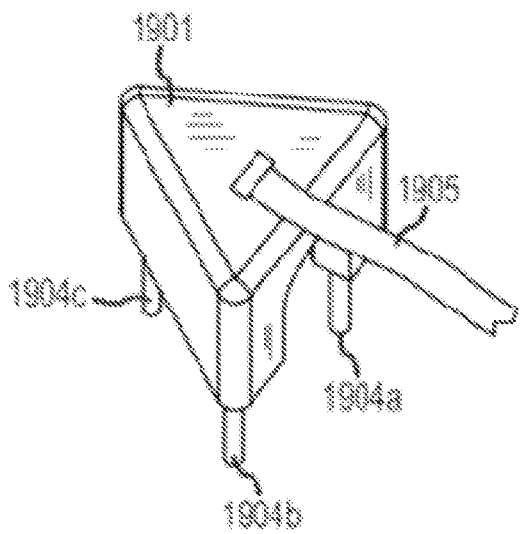
FIG. 19B illustrates another oblique view of the attachment of FIG. 19A.
Figure 20A:
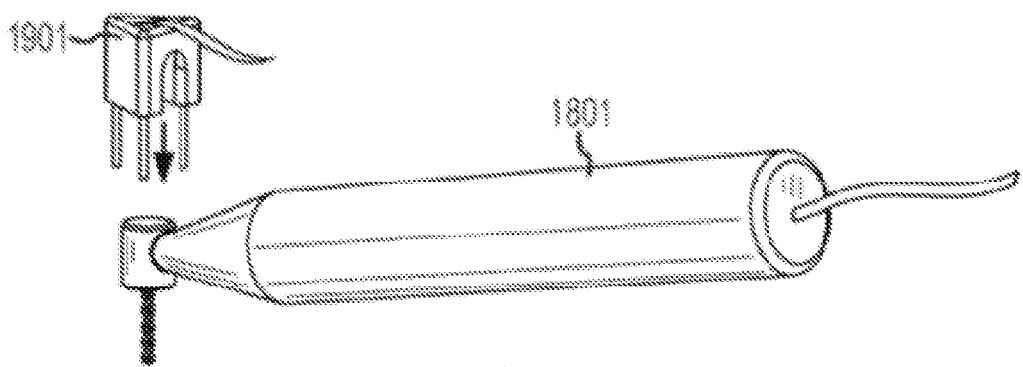
FIG. 20A illustrates the attachment of FIG. 19A in position to engage with the handpiece of FIG. 18.
Figure 20B:
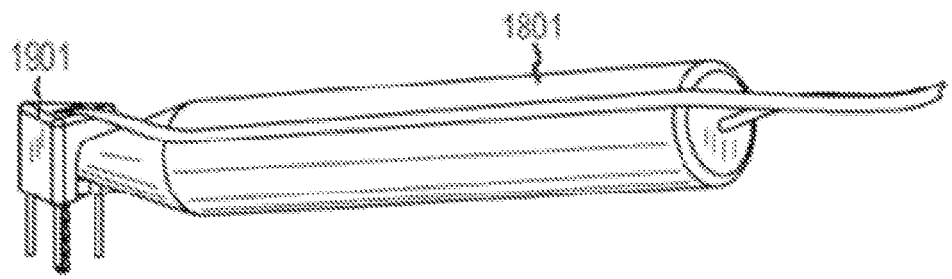
FIG. 20B illustrates the attachment of FIG. 19A engaged with the handpiece of FIG. 18.

FIGS. 19A and 19B illustrate oblique views of an attachment 1901 in accordance with embodiments of the invention, for use with a dental handpiece such as dental handpiece 1801. Attachment 1901 includes a fitting configured to engage with the dental handpiece. For example, attachment 1901 may define a cavity 1902 of a shape and size to snugly fit over the dental handpiece, and may also include a snap feature, a clamp, a setscrew, or another kind of device to mount attachment 1901 in fixed relation to the dental handpiece. Exemplary attachment 1901 also comprises a sensor system that includes three handpiece alignment sensors 1903a-c, portions of which are visible. When attachment 1901 is fixed to dental handpiece 1801, sensors 1903a-c are in spaced relationship to drill bit 1802. FIG. 20A shows attachment 1901 in position to engage with dental handpiece 1801, and FIG. 20B shows attachment 1901 engaged with dental handpiece 1801.

Referring to the embodiment of FIG. 19A, each of sensors 1903a-c includes a linearly movable portion 1904a-c and a sensing element that characterizes the position of the movable portion, as previously described. For example, the sensing elements may comprise linear encoders. In use, the sensors engage a surface and cooperate to provide data that characterize the depth and angular orientation of a drill comprised in the dental handpiece, in relation to the surface. For example, if the linear positions of all three movable portions are known, and the geometrical relationship of the sensors to the drill bit is known, then the depth and angular orientation of the drill bit in relation to a surface engaged by the sensors can be calculated from the sensor data.

Attachment 1901 also includes an electronic interface to communicate data to another system, for example over cable 1905 to computer implementation system 600 described above. The communicated data may be the raw sensor position readings, or may be an indication of the drill bit depth and angular orientation computed from the sensor position readings, or may be some other set of data sufficient to characterize the depth and angular orientation of drill bit 1802. The data may be communicated in analog or digital form. In some embodiments, attachment 1901 may include a standard interface such as a universal serial bus (USB) interface to communicate the sensor data. Attachment 1901 may include additional circuitry (not shown) for connecting sensors 1903a-c with the electronic interface and conditioning the sensor signals for transmission over the electronic interface.

Preferably, attachment 1901 is disposable. That is, a particular attachment 1901 may be used in relation to only one patient, and may be used only once in relation to the patient. More than one implant shaft may be prepared for the patient during a particular use session, but should additional implant shafts be prepared in another session, a different attachment 1901 is preferably used.

In preparing an implant site using attachment 1901, a user may fix attachment 1901 to a dental handpiece, and then drill an implant shaft at an implant site, using data from sensors 1903*a-c* to guide the drilling. For example, data from sensors 1903*a-c* may be processed to generate a display showing the position and angular orientation of a drill bit in relation to the desired implant shaft. Once drilling is complete, the user may remove attachment 1901 from the dental handpiece and dispose of it, so that a particular attachment 1901 is used in relation to only one patient.

Figure 21A:
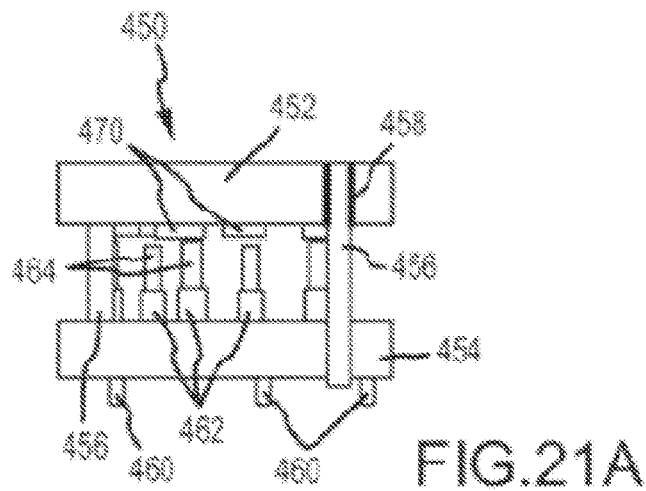
FIG. 21A is a side view of an alternative embodiment of the handpiece sensor assembly.
Figure 21B:
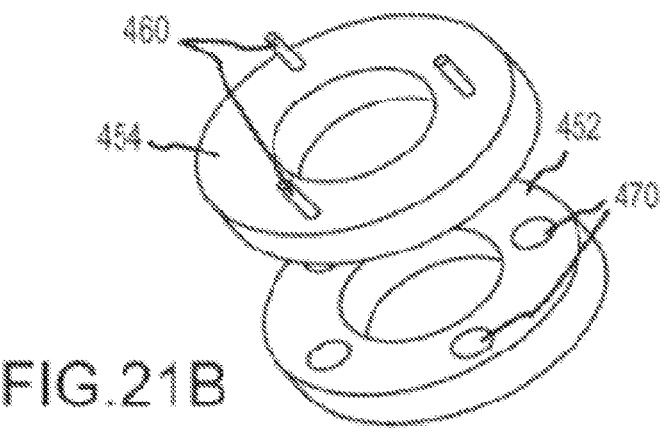
FIG. 21B is a perspective view of the lower surfaces of the lower and upper rings of the embodiment of FIG. 21A.
Figure 21C:
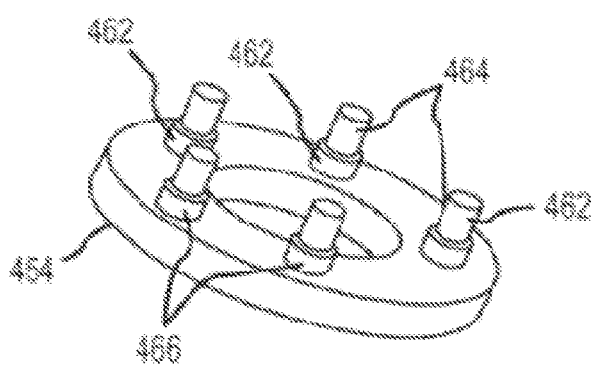
FIG. 21C is a perspective view of the upper surface of the lower ring of the embodiment of FIG. 21C.

FIGS. 21A-C illustrate an alternative embodiment of a sensor system 450 formed from a pair of planar rings 452 & 454 connected by guide pins 456 that extend upward from ring 454 to be slidably retained within guide channels 458 so that ring 452 can move toward and away from ring 454. As illustrated in FIG. 21A, two guide pins are shown, but more may be used. The rings are dimensioned to receive the dental drill head in their center, so that the drill shaft extends through the lower ring 454 and is concentric with the rings. Preferably, the upper ring 452 will produce an interference, or snap, fit around at least a portion of the head of the dental handpiece so that the upper ring 452 of the sensor system 450 moves with the drill.

Extending downward from the lower surface of ring 454 are alignment pins 460, which are dimensioned to insert into corresponding alignment structures in the planar reference surface of the workpiece guide. The three alignment pins 460 as shown in the figure are exemplary only, and a single pin, two pins or more than three pins may be used. Extending from the upper surface of ring 454 are sensor activator structures 462 which include a semi-compressible elastomer core 464 and a support base 466. Activator structures 462 serve the dual purposes of activating the sensors on the lower surface of ring 452 and providing a depth limiter for drilling. The height of the activator structures 462 will be selected to provide the desired separation between rings 452 and 454 to permit proper positioning of the drill tip at the pilot hole. Elastomer cores 464 may be telescopically retained within base 466, or they may be fixed within the base and the compressibility of the elastomeric material may be selected to allow the core to compress sufficiently to allow the drill to achieve its desired depth. As illustrated, there are five activator structures shown, however, as few as three such structures may be used, or more than five may be used. The number will correspond to the number of sensors in the upper ring.

As an alternative to the elastomer cores in the activator structures, pins formed from a rigid material (e.g., metal, plastic or polymer) may be telescopically received within the base portion. Bias springs located within the base will force the pins outward to contact the sensors while allowing them to be compressed as the drilling progresses.

Sensors 470 are located within the lower surface of the upper ring 452. The sensors may be fully embedded within the ring body or they may extend slightly downward from the surface. The number of sensors will preferably correspond with the number of activator structures 462 in the lower ring 454, e.g., as few as three may be used. Miniature force and pressure sensors are known and widely used in many fields including robotics, prosthetics, and other areas. Appropriate force sensors for use in the sensor system include piezoelectric sensors, thin film force sensors, MEMS sensors including, but not limited to, silicon microsensors, and other sensors as are known in the art. Conductive connectors for conveying the sensor signals to the computer are not shown, but will typically pass through the top or sides of the upper ring 452 and along the dental handpiece.

The sensor system shown in FIGS. 21A-21C produces signals from which angular orientation may be determined as well as depth. For angular orientation, a change in the relative signal levels of the plurality of sensors will indicate deviation from the desired angle. For depth, a combination of the known heights of the activator structures and the pressure level indicated by each sensor will permit determination of the drilling depth. The dimensions and compressibility of the activator structures are preferably selected to provide a mechanical stop to limit the drilling depth while allowing changes in pressure to be detected as the activator structures are compressed.

The embodiments disclosed herein are exemplary and are not to be construed as limiting the scope of the invention. Many variations of the methods and devices described herein are available to the skilled artisan without departing from the scope of the invention. For example, embodiments described above include sensors with linearly movable portions wherein the orientation of the drill is determined from the positions of the linearly movable portions, and also include pressure-based sensors. It will be recognized that other numbers and other kinds of sensors may be used within the scope of the appended claims. For example, sensors engaging a surface of the workpiece guide may provide data that characterize the angular orientation of the drill based on direct angular measurement or other techniques.

What is claimed is:

1. A system comprising:
a dental handpiece including a handpiece drill;
a workpiece guide adapted to be fixed to a dental arch of a patient in a known location in relation to the patient's dentition;
a sensor system located on the dental handpiece and including a plurality of moveable mechanical elements, wherein the moveable mechanical elements surround the handpiece drill and contact a known surface of the workpiece guide;
an image processor that receives an image of the patient's dentition;
a location system that receives data from the sensor system and determines, based at least in part on the data from the sensor system, a depth and an angular orientation of the handpiece drill in relation to the patient's dentition; and
a viewer that generates a display image at a computer display such that the generated display image comprises the image of the patient's dentition and a depiction of the depth and angular orientation of the handpiece drill relative to the patient's dentition as determined by the location system;
wherein the location system receives updated sensor data and determines based at least in part on the updated sensor data an updated depth and angular orientation of the handpiece drill in relation to the patient's dentition, and the viewer adjusts the generated display image to show the updated depth and angular orientation of the handpiece drill relative to the patient's dentition.

2. The system of claim 1, wherein each of the moveable mechanical elements includes a sensor tip such that the sensor tips are independently extensible relative to the dental handpiece and are adapted to contact the known surface of the workpiece guide, and wherein the data from the sensor system indicates the extensions of the sensor tips relative to the dental handpiece, and wherein the location system determines the depth and angular orientation of the handpiece drill based at least in part on the extension of each sensor tip.

3. The system of claim 1, wherein the generated display image further comprises a depiction of the depth and angular orientation of the handpiece drill relative to a desired implant shaft.

4. A system, comprising:
a dental handpiece including a handpiece drill;
an attachment for fixing to the dental handpiece, wherein the attachment comprises a sensor system that generates data usable to determine the position and angular orientation of the handpiece drill in relation to a reference surface engaged by the sensor system, and wherein the sensor system includes a plurality of moveable mechanical elements surrounding the handpiece drill;
a workpiece guide of a configuration to engage a dental arch of a patient in a known location in relation to the patient's dentition, the workpiece guide including the reference surface over an implant site and features for registering the sensor system to the workpiece guide;
a computer system comprising a processor and a display; and
an electronic interface that communicates the data from the sensor system to the computer system;
wherein in use the sensor system is registered to the features of the workpiece guide and the sensor system engages the known reference surface of the workpiece guide, and the computer system receives the data from the sensor system, determines the position and angular orientation of the handpiece drill in relation to the patient's dentition based at least in part on the data from the sensor system, and displays, on a display, a display image that depicts the position and angular orientation of the handpiece drill in relation to the patient's dentition.

5. The system of claim 4, wherein the sensor system includes a plurality of sensors, each of the sensors including one of the moveable mechanical elements and a sensing element that characterizes the position of the respective moveable mechanical element, and wherein determining the position and angular orientation of the handpiece drill in relation to a reference surface engaged by the sensor system comprises determining the position and angular orientation based at least in part on the positions of the movable mechanical elements.

6. The system of claim 4, wherein the display image further depicts the position and angular orientation of the handpiece drill in relation to a desired implant shaft.

7. A computerized system comprising:
a dental handpiece including a handpiece drill;
a workpiece guide adapted to be fixed to a dental arch of a patient in a known location in relation to the patient's dentition, wherein the workpiece guide comprises a reference surface;
an image processor that receives an image of the patient's dentition;
a sensor system mountable to the dental handpiece, the sensor system comprising a plurality of moveable mechanical elements surrounding the handpiece drill, wherein the sensor system is of a configuration such that during use, the moveable mechanical elements contact the reference surface of the workpiece guide;
a location system that receives data from the sensor system and determines, based at least in part on the data from the sensor system, a depth and angular orientation of the handpiece drill in relation to the patient's dentition; and
a viewer that generates a display image at a computer display such that the generated display image comprises the image of the patient's dentition and a depiction of the depth and angular orientation of the handpiece drill relative to the patient's dentition as determined by the location system;
wherein the location system receives updated sensor data and determines based at least in part on the updated sensor data an updated depth and angular orientation of the handpiece drill in relation to the patient's dentition, and the viewer adjusts the generated display image to show the updated depth and angular orientation of the handpiece drill relative to the patient's dentition.

8. The computerized system of claim 7, wherein each of the moveable mechanical elements includes a sensor tip such that the sensor tips are independently extensible relative to the dental handpiece and are adapted to contact the reference surface of the workpiece guide, and wherein the data from the sensor system indicates the extensions of the sensor tips relative to the dental handpiece, and wherein the location system determines the depth and angular orientation of the handpiece drill based at least in part on the extension of each sensor tip.

9. The computerized system of claim 7, wherein the generated display image further comprises a depiction of the depth and angular orientation of the handpiece drill relative to a desired implant shaft.

10. The computerized system of claim 7, wherein the sensor system is retrofittable to the dental handpiece.

* * * * *